United States Patent
Cui et al.

(10) Patent No.: US 9,345,688 B2
(45) Date of Patent: May 24, 2016

(54) KCNQ CHANNELS AS THERAPEUTIC TARGETS

(71) Applicants: Washington University, St. Louis, MO (US); The Research Foundation for The State University of New York, Albany, NY (US); Curators of the University of Missouri, Columbia, MO (US)

(72) Inventors: Jianmin Cui, Chesterfield, MO (US); Ira S. Cohen, Stony Brook, NY (US); Xiaoqin Zou, Columbia, MO (US)

(73) Assignees: Washington University, St. Louis, MO (US); The Research Foundation for The State University of New York, Albany, NY (US); Curators of the University of Missouri, Columbia, MO (US)

(*) Notice: Subject to any disclaimer, the term of this patent is extended or adjusted under 35 U.S.C. 154(b) by 0 days.

(21) Appl. No.: 14/211,813

(22) Filed: Mar. 14, 2014

(65) Prior Publication Data
US 2014/0303226 A1    Oct. 9, 2014

Related U.S. Application Data

(60) Provisional application No. 61/788,794, filed on Mar. 15, 2013.

(51) Int. Cl.
| | |
|---|---|
| A61K 31/4035 | (2006.01) |
| A61K 31/136 | (2006.01) |
| A61K 31/185 | (2006.01) |
| A61K 31/27 | (2006.01) |
| A61K 31/555 | (2006.01) |

(52) U.S. Cl.
CPC ........... *A61K 31/4035* (2013.01); *A61K 31/136* (2013.01); *A61K 31/185* (2013.01); *A61K 31/27* (2013.01); *A61K 31/555* (2013.01)

(58) Field of Classification Search
None
See application file for complete search history.

(56) References Cited

PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface).*
Jordan, V. C. (Nature Reviews: Drug Discovery, 2, 2003, 205-213).*
Website-ChemSpider ID: 550046, http://www.chemspider.com/Chemical-Structure.550046.html (2 pages) (2015).*
Website-ChemExper Chemical Directory, http://www.chemexper.com/search/cas/1324216.html (2 pages) (2015).*
Brown D.A., "Kv7 (KCNQ) Potassium Channels that are Mutated in Human Diseases", J Physiol 586(7):1781-1783 (2008).
Hernandez C.C. et al., "A Carboxy-Terminal Inter-Helix Linder as the Site of Phosphatidylinositol 4,5-Bisphosphate Action on Kv7 (M-Type) K+ Channels", J. Gen. Physiol. 132(3):361-381 (Aug. 25, 2008).
Li Y. et al., "KCNE1 Enhances Phosphatidylinositol 4,5-Bisphosphate (PIP2) Sensitivity of Iks to Modulate Channel Activity", Proc Natl Acad Sci USA 108(22):9095-1000 (May 31, 2011).
Missan S. et al., "Role of Kinases and G-Proteins in the Hyposmotic Stimulation of Cardiac Iks", Biochimica et Biophysica Acta 1758:1641-1652 (2006).
Sanguinetti M.C. et al., "Coassembly of KVLQT1 and Mink (IsK) Proteins to Form Cardiac IKs Potassium Channel", Nature 384:80-83 (Nov. 7, 1996).
Singh N.A. et al., "A Novel Potassium Channel Gene, KCNQ2, is Mutated in an Inherited Epilepsy of Newborns", Nature Genetics 18:25-29 (Jan. 1998).
Sun X. et al., "Regulation of Voltage-Activated K+ Channel Gating by Transmembrane B Subunits", Frontiers in Pharmacology 3(63) (10 pages) (Apr. 17, 2012).
Thomas A.M. et al., "Characterization of a Binding Site for Anionic Phospholipids on KCNQ1", J Biol Chem. 286 (3):2088-2100 (Jan. 21, 2011).
Wang H-S et al., "KCNQ2 and KCNQ3 Potassium Channel Subunits: Molecular Correlates of the M-Channel", Science 282:1890-1893 (Dec. 4, 1998).
Wang Q. et al., "Positional Cloning of a Novel Potassium Channel Gene: KVLQT1 Mutations Cause Cardiac Arrhythmias", Nature Genetics 12:17-23 (Jan. 1996).
Wu D. et al., "State-Dependent Electrostatic Interactions of S4 Arginines with E1 in S2 During Kv7.1 Activation", J. Gen. Physiol. 135(6):595-606, plus Supplemental Material (13 pages) (May 2010).
Zaydman M.A. et al., "Kv7.1 Ion Channels Require a Lipid to Couple Voltage Sensing to Pore Opening", Proc Natl Acad Sci USA 110(32)13180-13185 (Aug. 6, 2013).

* cited by examiner

*Primary Examiner* — Jeffrey S Lundgren
*Assistant Examiner* — William Lee
(74) *Attorney, Agent, or Firm* — Scully, Scott, Murphy & Presser, P.C.

(57) ABSTRACT

The present disclosure relates to methods and compositions for modulating the activity of KCNQ channels as a means for reducing the effects of aberrant KCNQ channel function associated with epilepsy, deafness and arrhythmias including but not limited to, Long-QT syndrome ("LQTS"), and atrial fibrillation. The present disclosure also relates to the discovery of certain regions of KCNQ channels that interact with various channel stimulating molecules such as, ATP, and $PIP_2$, as well as KCNQ channel domains that effect voltage dependant channel activation. The disclosure is also directed to the use of small molecules to modulate KCNQ channel activity in a cell. Moreover, the present disclosure relates to the therapeutic effects of treating a subject with modulators of KCNQ channel activity.

12 Claims, 14 Drawing Sheets
(11 of 14 Drawing Sheet(s) Filed in Color)

SEQUENCE LISTING

```
<160> NUMBER OF SEQ ID NOS: 36

<210> SEQ ID NO 1
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ1 protein S2-S3 linker domain

<400> SEQUENCE: 1

Ser Ala Gly Cys Arg Ser Lys Tyr Val Gly Leu Trp Gly Arg Leu Arg
1               5                   10                  15

Phe Ala Arg Lys Pro Ile Ser Ile
            20

<210> SEQ ID NO 2
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ2 protein S2-S3 linker domain

<400> SEQUENCE: 2

Ala Ala Gly Cys Cys Cys Arg Tyr Arg Gly Trp Arg Gly Arg Leu Lys
1               5                   10                  15

Phe Ala Arg Lys Pro Phe Cys Val
            20

<210> SEQ ID NO 3
<211> LENGTH: 26
<212> TYPE: PRT
<213> ORGANISM: Artificial Sequence
<220> FEATURE:
<223> OTHER INFORMATION: A therapeutic binding domain corresponding to a
``` segment of the KCNQ3 protein S2-S3 linker domain

<400> SEQUENCE: 3

Ala Ala Gly Cys Cys Cys Arg Tyr Lys Gly Trp Arg Gly Arg Leu Lys
1               5                   10                  15

Phe Ala Arg Lys Pro Leu Cys Met Leu Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: A therapeutic binding domain corresponding to a
      segment of the KCNQ4 protein S2-S3 linker domain

<400> SEQUENCE: 4

Arg Val Trp Ser Ala Gly Cys Cys Cys Arg Tyr Arg Gly Trp Gln Gly
1               5                   10                  15

Arg Phe Arg Phe Ala Arg Lys Pro Phe Cys Val Ile Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: A therapeutic binding domain corresponding to a
      segment of the KCNQ5 protein S2-S3 linker domain

<400> SEQUENCE: 5

Arg Ile Trp Ser Ala Gly Cys Cys Cys Arg Tyr Arg Gly Trp Gln Gly
1               5                   10                  15

Arg Leu Arg Phe Ala Arg Lys Pro Phe Cys Val Ile Asp
            20                  25

<210> SEQ ID NO 6
<211> LENGTH: 26
<212> TYPE: PRT
<213> ORGANISM: Artificial Sequence
<220> FEATURE:
<223> OTHER INFORMATION: A therapeutic binding domain corresponding to a
      segment of the KCNQ5 protein S2-S3 linker domain

<400> SEQUENCE: 6

Arg Met Leu His Val Asp Arg Gln Gly Gly Thr Trp Arg Leu Leu Gly
1               5                   10                  15

Ser Val Val Phe Ile His Arg Gln Glu Leu
            20                  25

<210> SEQ ID NO 7
<211> LENGTH: 26
<212> TYPE: PRT
<213> ORGANISM: Artificial Sequence
<220> FEATURE:
<223> OTHER INFORMATION: A therapeutic binding domain corresponding to a
      segment of the KCNQ2 protein S4-S5 domain

<400> SEQUENCE: 7

Arg Met Ile Arg Met Asp Arg Arg Gly Gly Thr Trp Lys Leu Leu Gly
1               5                   10                  15

Ser Val Val Tyr Ala His Ser Lys Glu Leu
            20                  25

```
<210> SEQ ID NO 8
<211> LENGTH: 27
<212> TYPE: PRT
<213> ORGANISM: Artificial Sequence
<220> FEATURE:
<223> OTHER INFORMATION: A therapeutic binding domain corresponding to a
      segment of the KCNQ3 protein S4-S5 domain

<400> SEQUENCE: 8

Arg Met Leu Arg Met Asp Arg Arg Gly Gly Thr Trp Lys Leu Leu Gly
1               5                   10                  15

Ser Ala Ile Cys His Ala His Ser Lys Glu Leu
            20                  25

<210> SEQ ID NO 9
<211> LENGTH: 26
<212> TYPE: PRT
<213> ORGANISM: Artificial Sequence
<220> FEATURE:
<223> OTHER INFORMATION: A therapeutic binding domain corresponding to a
      segment of the KCNQ4 or KCNQ5 protein S4-S5 domain

<400> SEQUENCE: 9

Arg Met Val Arg Met Asp Arg Arg Gly Gly Thr Trp Lys Leu Leu Gly
1               5                   10                  15

Ser Val Val Tyr Ala His Ser Lys Glu Leu
            20                  25

<210> SEQ ID NO 10
<211> LENGTH: 25
<212> TYPE: PRT
<213> ORGANISM: Artificial Sequence
<220> FEATURE:
<223> OTHER INFORMATION: A therapeutic binding domain corresponding to a
      segment of the KCNQ1 S6- C-terminal linker domain

<400> SEQUENCE: 10

Ile Leu Gly Ser Gly Phe Ala Leu Lys Val Gln Gln Lys Gln Arg Gln
1               5                   10                  15

Lys His Phe Asn Arg Gln Ile Pro Ala
            20                  25

<210> SEQ ID NO 11
<211> LENGTH: 25
<212> TYPE: PRT
<213> ORGANISM: Artificial Sequence
<220> FEATURE:
<223> OTHER INFORMATION: A therapeutic binding domain corresponding to a
      segment of the KCNQ2 S6- C-terminal linker domain

<400> SEQUENCE: 11

Ile Leu Gly Ser Gly Phe Ala Leu Lys Val Gln Glu Gln His Arg Gln
1               5                   10                  15

Lys His Phe Glu Lys Arg Arg Asn Pro
            20                  25

<210> SEQ ID NO 12
<211> LENGTH: 25
<212> TYPE: PRT
<213> ORGANISM: Artificial Sequence
<220> FEATURE:
<223> OTHER INFORMATION: A therapeutic binding domain corresponding to a
      segment of the KCNQ3 S6- C-terminal linker domain

<400> SEQUENCE: 12

Ile Leu Gly Ser Gly Leu Ala Leu Lys Val Gln Glu Gln His Arg Gln
```

```
1               5                   10                  15
Lys His Phe Glu Lys Arg Arg Lys Pro
            20                  25

<210> SEQ ID NO 13
<211> LENGTH: 25
<212> TYPE: PRT
<213> ORGANISM: Artificial Sequence
<220> FEATURE:
<223> OTHER INFORMATION: A therapeutic binding domain corresponding to a
      segment of the KCNQ4 S6- C-terminal linker domain

<400> SEQUENCE: 13

Ile Leu Gly Ser Gly Phe Ala Leu Lys Val Gln Glu Gln His Arg Gln
1               5                   10                  15

Lys His Phe Glu Lys Arg Arg Met Pro
            20                  25

<210> SEQ ID NO 14
<211> LENGTH: 25
<212> TYPE: PRT
<213> ORGANISM: Artificial Sequence
<220> FEATURE:
<223> OTHER INFORMATION: A therapeutic binding domain corresponding to a
      segment of the KCNQ5 S6- C-terminal linker domain

<400> SEQUENCE: 14

Ile Leu Gly Ser Gly Phe Ala Leu Lys Val Gln Glu Gln His Arg Gln
1               5                   10                  15

Lys His Phe Glu Lys Arg Arg Asn Pro
            20                  25

<210> SEQ ID NO 15
<211> LENGTH: 11
<212> TYPE: PRT
<213> ORGANISM: Artificial Sequence
<220> FEATURE:
<223> OTHER INFORMATION: A therapeutic binding domain corresponding to a
      segment of the KCNQ5 S6- C-terminal linker domain
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 15

Arg Xaa Xaa Xaa Xaa Arg Xaa His Arg Xaa Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: A therapeutic binding domain corresponding to a
      segment of the KCNQ2, KCNQ4 OR KCNQ5 protein(s) PIP2 binding
      domain
<220> FEATURE:
<221> NAME/KEY: misc_feature
<222> LOCATION: (2)..(5)
<223> OTHER INFORMATION: Xaa can be any naturally occurring amino acid
<220> FEATURE:
```

```
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 16

Arg Xaa Xaa Xaa Xaa Arg Xaa His Xaa Lys Xaa Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: A therapeutic binding domain corresponding to a
      segment of the KCNQ3 protein PIP2 binding domain
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 17

Arg Xaa Xaa Xaa Xaa Arg Xaa His Xaa Lys Xaa Lys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: A therapeutic binding domain corresponding to a
      segment of the KCNE1 protein

<400> SEQUENCE: 18

Arg Ser Lys Lys Leu Glu His Ser Asn
1               5

<210> SEQ ID NO 19
<211> LENGTH: 7
<212> TYPE: PRT
<213> ORGANISM: Artificial Sequence
<220> FEATURE:
<223> OTHER INFORMATION: A therapeutic binding domain corresponding to a
      segment of the KCNE1 protein PIP2 binding domain
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 19
```

```
Arg Xaa Lys Lys Xaa Xaa His
1               5

<210> SEQ ID NO 20
<211> LENGTH: 29
<212> TYPE: PRT
<213> ORGANISM: Artificial Sequence
<220> FEATURE:
<223> OTHER INFORMATION: A therapeutic binding domain corresponding to a
      segment of the KCNQ1 C-terminal domain

<400> SEQUENCE: 20

Pro Ala Ala Ala Ser Leu Ile Gln Thr Ala Trp Arg Cys Tyr Ala Ala
1               5                   10                  15

Glu Asn Pro Asp Ser Ser Thr Trp Lys Ile Tyr Ile Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: A therapeutic binding domain corresponding to a
      segment of the KCNQ2 C-terminal domain

<400> SEQUENCE: 21

Pro Ala Ala Gly Leu Ile Gln Ser Ala Trp Arg Phe Tyr Ala Thr Asn
1               5                   10                  15

Leu Ser Arg Thr Asp Leu His Ser Thr Trp Gln Tyr
            20                  25

<210> SEQ ID NO 22
<211> LENGTH: 27
<212> TYPE: PRT
<213> ORGANISM: Artificial Sequence
<220> FEATURE:
<223> OTHER INFORMATION: A therapeutic binding domain corresponding to a
      segment of the KCNQ3 C-terminal domain

<400> SEQUENCE: 22

Pro Ala Ala Glu Leu Ile Gln Ala Ala Trp Arg Tyr Tyr Ala Thr Asn
1               5                   10                  15

Pro Asn Arg Ile Asp Leu Val Ala Thr Trp Arg
            20                  25

<210> SEQ ID NO 23
<211> LENGTH: 28
<212> TYPE: PRT
<213> ORGANISM: Artificial Sequence
<220> FEATURE:
<223> OTHER INFORMATION: A therapeutic binding domain corresponding to a
      segment of the KCNQ4 C-terminal domain

<400> SEQUENCE: 23

Pro Ala Ala Asn Leu Ile Gln Ala Ala Trp Arg Leu Tyr Ser Thr Asp
1               5                   10                  15

Met Ser Arg Ala Tyr Leu Thr Ala Thr Trp Tyr Tyr
            20                  25

<210> SEQ ID NO 24
<211> LENGTH: 26
<212> TYPE: PRT
<213> ORGANISM: Artificial Sequence
<220> FEATURE:
<223> OTHER INFORMATION: A therapeutic binding domain corresponding to a
``` segment of the KCNQ5 C-terminal domain

<400> SEQUENCE: 24

Pro Ala Ala Asn Leu Ile Gln Cys Val Trp Arg Ser Tyr Ala Ala Asp
1               5                   10                  15

Glu Lys Ser Val Ser Ile Ala Thr Trp Lys
            20                  25

<210> SEQ ID NO 25
<211> LENGTH: 8
<212> TYPE: PRT
<213> ORGANISM: Artificial Sequence
<220> FEATURE:
<223> OTHER INFORMATION: A therapeutic binding domain corresponding to a
      segment of a KCNQ channel proteins ATP binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 25

Trp Arg Xaa Lys Xaa Xaa Xaa Arg
1               5

<210> SEQ ID NO 26
<211> LENGTH: 23
<212> TYPE: PRT
<213> ORGANISM: Artificial Sequence
<220> FEATURE:
<223> OTHER INFORMATION: A therapeutic binding domain corresponding to a
      segment of the KCNQ1 S2 domain

<400> SEQUENCE: 26

Thr Leu Phe Trp Met Glu Ile Val Leu Val Val Phe Phe Gly Thr Glu
1               5                   10                  15

Tyr Val Val Arg Leu Trp Ser
            20

<210> SEQ ID NO 27
<211> LENGTH: 22
<212> TYPE: PRT
<213> ORGANISM: Artificial Sequence
<220> FEATURE:
<223> OTHER INFORMATION: A therapeutic binding domain corresponding to a
      segment of the KCNQ2 S2 domain

<400> SEQUENCE: 27

Ala Leu Tyr Ile Leu Glu Ile Val Thr Ile Val Val Phe Gly Val Glu
1               5                   10                  15

Tyr Phe Val Arg Ile Trp
            20

<210> SEQ ID NO 28
<211> LENGTH: 22
<212> TYPE: PRT
<213> ORGANISM: Artificial Sequence
<220> FEATURE:
<223> OTHER INFORMATION: A therapeutic binding domain corresponding to a
      segment of the KCNQ3 S2 domain

<400> SEQUENCE: 28

Trp Leu Leu Leu Leu Glu Thr Phe Ala Ile Phe Ile Phe Gly Ala Glu
1               5                   10                  15

```
Phe Ala Leu Arg Ile Trp
            20

<210> SEQ ID NO 29
<211> LENGTH: 22
<212> TYPE: PRT
<213> ORGANISM: Artificial Sequence
<220> FEATURE:
<223> OTHER INFORMATION: A therapeutic binding domain corresponding to a
      segment of the KCNQ4 S2 domain

<400> SEQUENCE: 29

Cys Leu Leu Ile Leu Glu Phe Val Met Ile Val Val Phe Gly Leu Glu
1               5                   10                  15

Tyr Ile Val Arg Val Trp
            20

<210> SEQ ID NO 30
<211> LENGTH: 22
<212> TYPE: PRT
<213> ORGANISM: Artificial Sequence
<220> FEATURE:
<223> OTHER INFORMATION: A therapeutic binding domain corresponding to a
      segment of the KCNQ5 S2domain

<400> SEQUENCE: 30

Cys Leu Leu Ile Leu Glu Phe Val Met Ile Val Val Phe Gly Leu Glu
1               5                   10                  15

Phe Ile Ile Arg Ile Trp
            20

<210> SEQ ID NO 31
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ1 S4 domain

<400> SEQUENCE: 31

Ala Thr Ser Ala Ile Arg Gly Ile Arg Phe Leu Gln Ile Leu Arg Met
1               5                   10                  15

Leu His Val Asp Arg Gln Gly Gly
            20

<210> SEQ ID NO 32
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ2 S4 domain

<400> SEQUENCE: 32

Ala Thr Ser Ala Leu Arg Ser Leu Arg Phe Leu Gln Ile Leu Arg Met
1               5                   10                  15

Ile Arg Met Asp Arg Arg Gly Gly
            20

<210> SEQ ID NO 33
<211> LENGTH: 23
<212> TYPE: PRT
<213> ORGANISM: Artificial Sequence
<220> FEATURE:
<223> OTHER INFORMATION: A therapeutic binding domain corresponding to a
``` segment of the KCNQ3 S4 domain

<400> SEQUENCE: 33

Ala Thr Ser Leu Arg Ser Leu Arg Phe Leu Gln Ile Leu Arg Met Leu
1               5                   10                  15

Arg Met Asp Arg Arg Gly Gly
            20

<210> SEQ ID NO 34
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ4 S4 domain

<400> SEQUENCE: 34

Ala Thr Ser Ala Leu Arg Ser Met Arg Phe Leu Gln Ile Leu Arg Met
1               5                   10                  15

Val Arg Met Asp Arg Arg Gly Gly
            20

<210> SEQ ID NO 35
<211> LENGTH: 24
<212> TYPE: PRT
<213> ORGANISM: Artificial Sequence
<220> FEATURE:
<223> OTHER INFORMATION: A therapeutic binding domain corresponding to a
      segment of the KCNQ4 S4 domain

<400> SEQUENCE: 35

Ala Thr Ser Ala Leu Arg Ser Leu Arg Phe Leu Gln Ile Leu Arg Met
1               5                   10                  15

Val Arg Met Asp Arg Arg Gly Gly
            20

<210> SEQ ID NO 36
<211> LENGTH: 10
<212> TYPE: PRT
<213> ORGANISM: Artificial Sequence
<220> FEATURE:
<223> OTHER INFORMATION: A therapeutic binding domain corresponding to a
      segment of a KCNQ channel protein voltage gating domain
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid

<400> SEQUENCE: 36

Arg Xaa Xaa Arg Xaa Xaa Xaa Xaa Xaa Arg
1               5                   10

KCNQ CHANNELS AS THERAPEUTIC TARGETS

CROSS REFERENCE TO RELATED APPLICATIONS

This application claims priority from U.S. Provisional Application No. 61/788,794, filed Mar. 15, 2013, the entire contents of which are incorporated herein by reference.

GOVERNMENT INTEREST

The present disclosure was made with government support under grant numbers HL70393, NS060706, HL094410, and GM088517 awarded by the National Institutes of Health. The government has certain rights in the disclosure.

INCORPORATION BY REFERENCE OF SEQUENCE LISTING

The Sequence Listing in the ASCII text file, named as 29866_sequencelisting.txt of 16 KB, created on Mar. 14, 2014, and submitted to the United States Patent and Trademark Office via EFS-Web, is incorporated herein by reference.

FIELD OF THE DISCLOSURE

The present disclosure relates to methods and compositions for modulating the activity of KCNQ channels as a means for reducing the effects of aberrant KCNQ channel function associated with epilepsy, deafness and arrhythmias including but not limited to, long-QT syndrome ("LQTS"), and atrial fibrillation. In particular, the present disclosure relates to the discovery of certain regions of KCNQ channels that interact with various channel stimulating molecules such as, adenosine-5'-triphosphate ("ATP"), and phosphatidylinositol 4,5-bisphosphate ($PIP_2$), as well as KCNQ channel domains that effect voltage dependant channel activation. The disclosure is also directed to the use of small molecules to modulate KCNQ channel activity. Moreover, the present disclosure relates to the therapeutic effects of treating a subject with modulators of KCNQ channel activity.

BACKGROUND OF THE DISCLOSURE

Voltage activated KCNQ potassium ("$K^+$") channels, provide the molecular basis for slowly activating delayed-rectifier $K^+$ ($I_{Ks}$) current in the heart, M-currents in neurons which regulate the firing rate of neurons in the central nervous system and potassium currents in cochlear hair cells. $I_{Ks}$, is composed of an $\alpha$ subunit, KCNQ1, and a $\beta$ subunit, KCNE1 (also known as minK) (see Sanguinetti, M C. et al., *Nature* (1996) 384: 80-83.), while heteromultimers of KCNQ2, KCNQ3 and KCNQ5 subunits form the basis for the M-channel and KCNQ4 channels form $K^+$ currents of the cochlear outer hair cells and vestibular utricle in the inner ear. Mutations within the KCNQ channel proteins, KCNQ1-5 (otherwise known as Kv7.1-5 or KvLQT1-5) are associated with cardiac arrhythmias (see Wang, Q. et al., *Nat. Genetics* (1996) 12:17-23; Tester, D J. et al., *Heart Rhythm.* (2005) 2: 507-517), epilepsy (see Brown, D A., *J. Physiology* (2008) 586: 1781-1783; Singh, N A. et al., *Nat. Genetics* (1998) 18:25-29) and deafness (see Brown D A. (2008)).

The crystal structures of several voltage-gated potassium channels have been elucidated and extensively studied (see Jiang, Y. et al., *Nature* (2003) 423:33-41; Long S B. et al *Science.* (2005) 309: 897-908), however structural modeling of KCNQ channels is incomplete. Although KCNQ channels are structurally similar to other voltage-gated K+ channels, the crystal structure has not yet been solved leading to conflicting results in the literature regarding the characterization of essential PIP2 and ATP binding domains as well as the voltage dependant activation motifs. See Thomas, A M. et al., *J. Biol. Chem.* (2011) 286(3):2088-100; Hernandez, C C. et al., *J. Gen. Physiol.* (2008) 132: 361-381).

SUMMARY OF THE DISCLOSURE

The present disclosure provides a method for modulating KCNQ channel activity of a cell. In an embodiment of the present disclosure the KCNQ channel activity of a cell is increased by contacting the cell with an agent that binds to a portion of a KCNQ channel, including but not limited to, KCNQ1, KCNQ2, KCNQ3, KCNQ4, KCNQ5, or KCNE1 in an amount effective to increase KCNQ channel activity of a cell. In certain embodiments, the agent is a small molecule including but not limited to C28 and C4. In an embodiment of the present disclosure the KCNQ channel activity of a cell is decreased by contacting the cell with an agent that binds to a portion of a KCNQ channel, including but not limited to, KCNQ1, KCNQ2, KCNQ3, KCNQ4, KCNQ5, or KCNE1 in an amount effective to decrease KCNQ channel activity of a cell. In certain embodiments, the agent is a small molecule including but not limited to C29.

In other embodiments, the small molecule binds to a KCNQ channel or subunit thereof contacting, at least one of the following amino acid sequences or a fragment or segment thereof; a non-limiting example of said amino acid sequence corresponds with the S2-S3 linker domain of human, rat, mouse, or rabbit KCNQ1 (amino acid residues 177-200), KCNQ2 (amino acid residues 147-170), KCNQ3 (amino acid residues 166-191), KCNQ4 (amino acid residues 150-178), KCNQ5 (amino acid residues 178-206) including variations or segments thereof.

In another embodiment the small molecule binds to a KCNQ channel or subunit thereof, contacting at least one of the following amino acid sequences or a fragment or segment thereof; a non-limiting example of said amino acid sequence corresponds with the S4-S5 linker domain of human, rat, mouse, or rabbit KCNQ1 (amino acid residues 237-262), KCNQ2 (amino acid residues 207-232), KCNQ3 (amino acid residues 225-250), KCNQ4 (amino acid residues 213-238), KCNQ5 (amino acid residues 241-266) including variations or segments thereof.

In yet another embodiment the small molecule binds to a KCNQ channel or subunit thereof, contacting at least one of the following amino acid sequences or a fragment or segment thereof; a non-limiting example of said amino acid sequence corresponds with the S6-C-terminal linker domain of human, rat, mouse, or rabbit KCNQ1 (amino acid residues 346-370), KCNQ2 (amino acid residues 311-335), KCNQ3 (amino acid residues 339-363), KCNQ4 (amino acid residues 317-341), KCNQ5 (amino acid residues 345-369) including variations or segments thereof.

In yet another embodiment the small molecule binds to a KCNE1 subunit of the $I_{Ks}$ channel by contacting at least one of the following amino acid sequences or a fragment or segment thereof; a non-limiting example of said amino acid sequence is amino acid residues 67-73 of human, rat, mouse, or rabbit KCNE1.

In yet another embodiment the small molecule binds to a KCNQ channel or subunit thereof, contacting at least one of the following amino acid sequences or a fragment or segment thereof; a non-limiting example of such an amino acid sequence corresponds with the C-terminal domain of human, rat, mouse, or rabbit KCNQ1 (amino acid residues 369-407), KCNQ2 (amino acid residues 334-372), KCNQ3 (amino acid residues 362-400), KCNQ4 (amino acid residues 340-378), KCNQ5 (amino acid residues 368-404) including variations or segments thereof.

In yet another embodiment the small molecule binds to a KCNQ channel or subunit thereof, contacting at least one of the following amino acid sequences or a fragment or segment thereof; and modulates the interaction between the S2 and S4 domain of a KCNQ protein. The amino acid sequence(s) that correspond with the S2 domain of human, rat, mouse, or rabbit KCNQ1 are amino acid residues 155-177, for KCNQ2 are amino acid residues 125-146, for KCNQ3 are amino acid residues 144-165, for KCNQ4 are amino acid residues 131-152, KCNQ5 are amino acid residues 159-180, including variations or segments thereof. The S4 domain of human, rat, mouse, or rabbit KCNQ1 includes amino acid residues 223-246, the S4 domain of human, rat, mouse, or rabbit KCNQ2 includes amino acid residues 193-216, the S4 domain of human, rat, mouse, or rabbit KCNQ3 includes amino acid residues 212-234, the S4 domain of human, rat, mouse, or rabbit KCNQ4 includes (amino acid residues 199-222), and the S4 domain of human, rat, mouse, or rabbit KCNQ5 includes (amino acid residues 227-250) including variations or segments thereof.

Small molecules that bind to homologs, analogs and fragments of these amino acid sequences are also contemplated by the present disclosure as modulators of KCNQ channel activity.

In an embodiment of the disclosure, the cell is a neural cell, including but not limited to a neuron. In another embodiment, the cell is a cardiac cell, including but not limited to, a myocyte. In another embodiment, the cell is an outer hair cell of the cochlear.

In certain aspects of the present disclosure is directed to methods and compositions for modulating KCNQ channel activity in a subject in need thereof, by administering an effective amount of an agent that modulates the activity of a KCNQ channel or a subunit thereof. The present disclosure provides specific compositions containing at least one KCNQ channel binding molecule that modulates at least one KCNQ channel-mediated biological activity in an organism, including humans.

In one embodiment of the present disclosure the composition is a peptide that binds a KCNQ channel or a subunit thereof. In yet another embodiment of the present disclosure, said composition is a small molecule that functions in the same manner as a KCNQ channel effector, including but not limited to ATP, or $PIP_2$ to modulate KCNQ channel activity. In yet another embodiment, the agent is a nucleic acid. The nucleic acid may be an siRNA, or shRNA. Nucleic acid molecules coding for any peptide that will interact with any of the amino acid sequences referenced herein, the expression vectors which include any of such nucleic acid molecules, as well as related host cells containing such nucleotide sequences or vectors, are also contemplated by the present disclosure.

These and other embodiments of the disclosure will be readily apparent to those of ordinary skill in view of the disclosure herein

BRIEF DESCRIPTION OF DRAWINGS

The file of this patent contains at least one drawing executed in color. Copies of this patent with color drawing(s) will be provided by the Patent and Trademark Office upon request and payment of the necessary fee.

Figure 14:
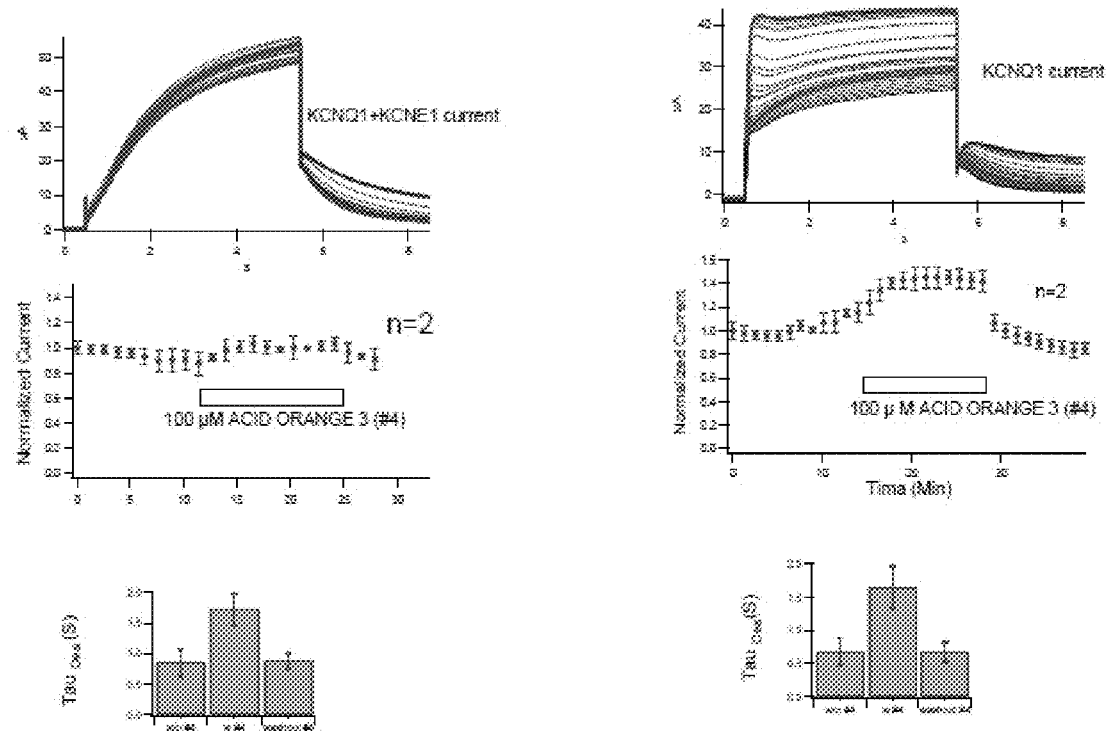

FIG. 14. Small molecule C4 (Acid Orange 3(#4)) modulates KCNQ1 channel activity. The effects of C4 on KCNQ channels alone (right) and $I_{Ks}$ channels (left). The upper panel shows raw currents through KCNQ channels where voltage was stepped from a holding potential of −80 to +40 mV. The middle panel reveals the time dependence of current amplitude after the drug is applied. The lower panel shows the time constants (Tau) exponential fit to channel deactivation

DETAILED DESCRIPTION OF THE DISCLOSURE

Ion channels permit flows of selective ions across cell membranes and regulate the membrane potential and the duration of action potentials, thereby controlling many basic biological processes such as contractions of cardiac, skeletal and smooth muscles and transport of nutrients and hormones. See Zaydman, M A. et al., *Chem. Rev.* 112:6319-6333. (2012).

Voltage activated KCNQ K$^+$ channels, KCNQ1-5 (also known as Kv7.1-5), are the molecular basis of $I_{Ks}$ currents in the heart, M-currents in many types of neurons, and K$^+$ currents in cochlear hair cells that regulate the cardiac action potential duration, neuronal discharge and synaptic transmission, and endolymph potassium homeostasis; mutations of these channel proteins are associated with cardiac arrhythmias, epilepsy and deafness. See Hill, B. *Ion Channels of Excitable Membranes*. 3$^{rd}$ ed. (2001). The slowly activating delayed-rectifier potassium current, $I_{Ks}$, is essential for the termination of cardiac action potentials and the maintenance of a normal heart rhythm. See Hill (2001). The $I_{Ks}$ channel is co-assembled by KCNQ1 and KCNE1 subunits. KCNQ1 is also referred to as Kv7.1 or KvLQT1, and KCNE1 is also known as minK. The α-subunit, KCNQ1, forms the conductance pore of $I_{Ks}$. The β-subunit, KCNE1, is an auxiliary protein that associates with and modulates the activity of KCNQ1. See Sun, X., et al., *Front. Pharmacology.* 3:63 (2012). These physiologically important channels all require PIP$_2$ in order to open, and the cardiac $I_{Ks}$ channel, formed by KCNQ1 and auxiliary subunit KCNE1 (see Sanguinetti et al. (1996)), also requires intracellular ATP for activation. Although PIP$_2$ and ATP are vital for the function of KCNQ channels, the molecular mechanisms of regulation by these signaling molecules are not clear; central questions such as the location and identity of PIP$_2$ and ATP binding sites and how these molecules alter channel function after binding still remain unclear. Previous studies and our data show that a number of mutations in KCNQ1 that are associated with long-QT syndrome (LQTS). Applicants' disclosure reveals that a reduction in $I_{Ks}$ channel activity by altering PIP$_2$ or ATP sensitivity leads to LQTS and provides the methodological basis for PIP$_2$ and ATP mediated regulation of KCNQ channels in their native cells.

KCNQ1 alone can form a functional voltage-gated potassium (Kv) channel. Kv channels are formed by the co-assembly of four α-subunits, each consisting of six transmembrane helices (S1-S6). The first four helices (S1-S4) form the voltage-sensing domain (VSD) and S5-S6 form the pore domain (PD). The S4 segment contains conserved basic residues. Membrane depolarization exerts force on these charged residues, moving S4 outward, which then induce the opening of the pore. To date, the crystal structure of full-length KCNQ1 has not been solved.

Mutations in the KCNQ1 gene are associated with long-QT syndrome, a congenital disorder that is characterized by a prolongation of the QT interval on electrocardiograms (ECGs), and increase the risk of sudden death from cardiac arrhythmias. The reduction of the $I_{Ks}$ currents by these mutations prolongs ventricular action potentials, thereby the QT interval. The $I_{Ks}$ channel therefore serves as a valuable drug target and the potentiators of $I_{Ks}$ can be used for treating cardiovascular diseases. During Kv channel formation, four subunits co-assemble to form a tetrameric complex with a central pore built from the PDs of all four subunits and the four VSDs located peripheral to the central pore. Voltage dependent activation involves three general molecular events: 1) VSD movements from the resting state to the activated state in response to membrane depolarization, 2) propagation of VSD activation to the PD through the interactions between VSD and PD, known as coupling, and 3) pore opening. See Tombola, F., et al. *Annu. Rev. Cell Dev. Biol.* 22:23-52. (2006).

The present disclosure elucidates the molecular mechanism governing KCNQ channel activity and shows that PIP$_2$ is not required for VSD movements but is required for the coupling between VSD and PD, and that ATP directly binds to KCNQ1 for channel activation. Thus, the present disclosure identifies and isolates the essential domains within KCNQ channels that govern channel activity, including but not limited to, voltage activation, PIP$_2$ binding and ATP binding. Therefore, methods and compositions for modulating the activity of KCNQ channels are provided as a means for treating a subject in need thereof.

Cardiac arrhythmias result from an increase in the duration of the ventricular action potential. This increase in ventricular action potential induces LQTS, which leads to a type of arrhythmia called torsade de pointes resulting in sudden death. In a small number of cases it is inherited, while in the vast majority it is acquired due to pharmacotherapy. This side effect of pharmacotherapy has removed promising drug candidates from market consideration and remains a serious concern with others that are currently in use. $I_{Ks}$ exists in mammalian atrial and ventricular myocytes providing for the repolarization of cardiac action potential. Atrial Fibrillation (AF) is an arrhythmia that has become increasingly prevalent in our aging population, and repolarization of the atrial action potential is in part due to $I_{Ks}$.

Novel targets of the present disclosure, which encompass regions of the $I_{Ks}$ channel, have been defined herein and used to create novel therapeutic approaches to treating LQTS. Blockers of this same channel have therapeutic potential for a common arrhythmia of the atrium, atrial fibrillation said blockers include but are not limited to 2-[4-(3,4-Dimethylphenoxy)phenyl]-1,3-dioxoisoindoline-5-carboxylic acid (C29). As, the α-subunit of the $I_{Ks}$ channel belongs to the KCNQ family and the M-current is composed of heteromultimers of three other members of the KCNQ family (KCNQ2, 3 and/or KCNQ5) and one of the K$^+$ channels in the ear is composed of KCNQ4, and thus the therapeutic agents of the present disclosure are also effective in treating epilepsy and congenital deafness, respectively.

Particularly, useful compositions for modulating KCNQ channels include, but are not limited to, disodium; 3-[[4-hydroxy-9,10-dioxo-2-(4-sulfonatoanilino)anthracen-1-yl]amino]benzenesulfonate (C28), bis(2-pyridylthio)zinc 1,1'-dioxide (zinc pyrithione) and ethyl N-[2-amino-4-[(4-fluorophenyl)methylamino]phenyl]carbamate (Retigabine).

The novel targets of the present disclosure encompass regions of KCNQ2-5 proteins and the channels composed thereof. Thus, agonists of channels containing KCNQ2-5 are used to alleviate the physiological conditions associated with KCNQ channel dysfunction via the use of therapeutic agents that act to enhance channel function, a non-limiting example is the compound; sodium; 2-anilino-5-(2,4-dinitroanilino) benzenesulfonate (C4), which can be used to treat diseases including, epilepsy and deafness. See FIG. 14.

Therapeutic Targets

According to the present disclosure there are small molecules that modulate KCNQ channel activity of a cell. In the present disclosure the small molecules modulate KCNQ channel activity of a cell by contacting a portion of a KCNQ channel, including but not limited to, KCNQ1, KCNQ2, KCNQ3, KCNQ4, KCNQ5, or KCNE1. In the present disclosure an effective amount of a small molecule will increase or decrease KCNQ channel activity. Non-exclusive measures of KCNQ channel activity include the ability of KCNQ channels or subunits thereof to bind effectors thereof, or the KCNQ channels ability to pass a current.

In one aspect, the agents of the present disclosure modulate KCNQ channel activity by interacting with the amino acid sequence that corresponds with the S2-S3 linker domain of human, rat, mouse, or rabbit KCNQ1 (amino acid residues 177-200) for example, SAGCRSKYVGLWGRLRFARKPISI (SEQ ID NO:1); KCNQ2 (amino acid residues 147-170) for example, AAGCCCRYRGWRGRLKFARKPFCV (SEQ ID NO:2); KCNQ3 (amino acid residues 166-191) for example, AAGCCCRYKGWRGRLKFARKPLCMLD (SEQ ID NO:3); KCNQ4 (amino acid residues 150-178) for example, RVWSAGCCCRYRGWQGRFRFARKPFCVID (SEQ ID NO:4); KCNQ5 (amino acid residues 178-206) for example, RIWSAGCCCRYRGWQGRLRFARKPFCVID (SEQ ID NO:5).

In one aspect of the current disclosure, the agents modulate KCNQ channel activity by interacting with an amino acid sequence corresponds with the S4-S5 domain of human, rat, mouse, or rabbit KCNQ1 (amino acid residues 237-262) for example, RMLHVDRQGGTWRLLGSVVFIHRQEL (SEQ ID NO: 6); KCNQ2 (amino acid residues 207-232) for example, RMIRMDRRGGTWKLLGSVVYAHSKEL (SEQ ID NO: 7); KCNQ3 (amino acid residues 225-250) for example, RMLRMDRRGGTWKLLGSAICHAHSKEL (SEQ ID NO: 8); KCNQ4 (amino acid residues 213-238) for example, RMVRMDRRGGTWKLLGSVVYAHSKEL (SEQ ID NO: 9); KCNQ5 (amino acid residues 241-266) for example, RMVRMDRRGGTWKLLGSVVYAHSKEL (SEQ ID NO:9) including variations or segments thereof.

In one aspect, the agents of the present disclosure modulate KCNQ channel activity by interacting with an amino acid sequence that corresponds with the S6-C-terminal linker domain of human, rat, mouse, or rabbit KCNQ1 (amino acid residues 346-370) for example ILGSGFALKVQQKQRQKHFNRQIPA (SEQ ID NO: 10); KCNQ2 (amino acid residues 311-335) for example, ILGSGFALKVQEQHRQKHFEKRRNP (SEQ ID NO: 11); KCNQ3 (amino acid residues 339-363) for example, ILGSGLALKVQEQHRQKHFEKRRKP (SEQ ID NO: 12); KCNQ4 (amino acid residues 317-341) for example ILGSGFALKVQEQHRQKHFEKRRMP (SEQ ID NO: 13); KCNQ5 (amino acid residues 345-369) for example, ILGSGFALKVQEQHRQKHFEKRRNP (SEQ ID NO: 14) including variations or segments thereof.

A preferred modulator of KCNQ channel activity of the present disclosure is a small molecule that interacts with the amino acid domain within the KCNQ1 protein encompassing the sequence $RXXXXXRX_{62}HRX_{94}K$ (SEQ ID NO: 15), wherein $X_n$ can be any amino acid which includes:

A=Ala=Alanine
R=Arg=Arginine
N=Asn=Asparagine
D=Asp=Aspartate
B=Asx=Asparagine or Aspartate
C=Cys=Cysteine
Q=Gln=Glutamine
E=Glu=Glutamate
Z=Glx=Glutamine or Glutamate
G=Gly=Glycine
H=His=Histidine
I=Ile=Isoleucine
L=Leu=Leucine
K=Lys=Lysine
F=Phe=Phenylalanine
P=Pro=Proline
S=Ser=Serine
T=Thr=Threonine
W=Trp=Tryptophan
Y=Tyr=Tyrosine
V=Val=Valine Preferably, $X_n$ are those amino acids that are homologs of the native residues found in the KCNQ channel protein.

More preferably, $X_n$ are those amino acids found in the native sequence of a vertebrate KCNQ channel protein.

A preferred modulator of KCNQ channel activity of the present disclosure is a small molecule that interacts with the amino acid domain within the KCNQ2, KCNQ4 OR KCNQ5 protein encompassing the sequence $RXXXXRX_{62}HXKX_{88}K$ (SEQ ID NO: 16).

A preferred modulator of KCNQ channel activity of the present disclosure is a small molecule that interacts with the amino acid domain within the KCNQ3 protein encompassing the sequence $RXXXXRX_{61}HXKX_{98}K$ (SEQ ID NO: 17).

Yet another preferred modulator of KCNQ channel activity is a small molecule that interacts with the amino acid residues within the KCNE1 protein encompassing amino acid residues 67-75 of human, rat, mouse, or rabbit KCNE1, for example RSKKLEHSN (SEQ ID NO. 18).

A preferred modulator of KCNQ channel activity of the present disclosure is a small molecule that interacts with the amino acid domain within the KCNE1 protein encompassing the sequence RXKKXXH (SEQ ID NO: 19).

In one aspect, the agents of the present disclosure modulate KCNQ channel activity by interacting with an amino acid sequence that corresponds with the C-terminal domain of human, rat, mouse, or rabbit KCNQ1 (amino acid residues 369-397) for example, PAAASLIQTAWRCYAAENPDSSTWKIYIR (SEQ ID NO: 20); KCNQ2 (amino acid residues 335-362) for example PAAGLIQSAWRFYATNLSRTDLHSTWQY (SEQ ID NO: 21); KCNQ3 (amino acid residues 363-389) for example PAAELIQAAWRYYATNPNRIDLVATWR (SEQ ID NO: 22); KCNQ4 (amino acid residues 341-368) for example, PAANLIQAAWRLYSTDMSRAYLTATWYY (SEQ ID NO: 23); KCNQ5 (amino acid residues 369-394) for example, PAANLIQCVWRSYAADEKSVSIATWK (SEQ ID NO: 24) including variations or segments thereof.

A preferred modulator of KCNQ channel activity of the present disclosure is a small molecule that interacts with the amino acid domain within a KCNQ protein encompassing the sequence $WRX_{12}KXXXR$ (SEQ ID NO: 25).

In one aspect, the agents of the present disclosure modulate KCNQ channel activity by interacting with an amino acid sequence that modulates the interaction between the S2 and S4 domain of a KCNQ protein. Non limiting examples of this domain include, the amino acid sequence that corresponds with the S2 domain of human, rat, mouse, or rabbit KCNQ1 comprises amino acid residues 155-177, TLFWMEIVLVVFFGTEYVVRLWS (SEQ ID NO: 26); KCNQ2 (amino acid residues 125-146) for example, ALYILEIVTIVVF-GVEYFVRIW (SEQ ID NO: 27); KCNQ3 (amino acid residues 144-165) for example, WLLLLETFAIFIFGAEFAL-RIW (SEQ ID NO: 28); KCNQ4 (amino acid residues 131-152) for example, CLLILEFVMIVVFGLEYIVRVW (SEQ ID NO: 29); KCNQ5 (amino acid residues 159-180) for example, CLLILEFVMIVVFGLEFIIRIW (SEQ ID NO: 30); the amino acid domain that comprises the S4 domain of human, rat, mouse, or rabbit KCNQ1 is amino acid residues 223-246, ATSAIRGIRFLQILRMLHVDRQGG (SEQ ID NO: 31), KCNQ2 (amino acid residues 193-216) for example, ATSALRSLRFLQILRMIRMDRRGG (SEQ ID NO: 32); KCNQ3 (amino acid residues 212-234) for example, ATSLRSLRFLQILRMLRMDRRGG (SEQ ID NO: 33); KCNQ4 (amino acid residues 199-222) for example, ATSALRSMRFLQILRMVRMDRRGG (SEQ ID NO: 34); KCNQ5 (amino acid residues 227-250) for example, ATSALRSLRFLQILRMVRMDRRGG (SEQ ID NO: 35), including variations or segments thereof.

A preferred modulator of KCNQ channel activity of the present disclosure is a small molecule that interacts with the amino acid domain within a KCNQ protein, which includes the sequence RXXRXXXXXR (SEQ ID NO: 36).

A preferred modulator of KCNQ channel activity interacts with an amino acid sequence encompassing any of the following amino acid residues R228, R231 and R237 that prevents interaction with amino acid E160 or D160 of a KCNQ protein.

A preferred modulator of KCNQ channel activity interacts with an amino acid sequence encompassing any of the following amino acid residues R198, R201 and R207 that prevents interaction with amino acid E130 of a KCNQ protein.

A preferred modulator of KCNQ channel activity interacts with an amino acid sequence encompassing any of the following amino acid residues R198, R201 and R207 that prevents interaction with amino acid E130 of a KCNQ protein.

A preferred modulator of KCNQ channel activity interacts with an amino acid sequence encompassing any of the following amino acid residues R216, R219 and R225 that prevents interaction with amino acid E149 of a KCNQ protein.

A preferred modulator of KCNQ channel activity interacts with an amino acid sequence encompassing any of the following amino acid residues R204, R207 and R213 that prevents interaction with amino acid E136 of a KCNQ protein.

A preferred modulator of KCNQ channel activity interacts with an amino acid sequence encompassing any of the following amino acid residues R232, R235 and R241 that prevents interaction with amino acid E1164 of a KCNQ protein.

Small molecules that bind to homologs, analogs and fragments of these amino acid sequences are also contemplated by the present disclosure as modulators of KCNQ channel activity.

In an embodiment of the disclosure, the cell is a neural cell, including but not limited to, a neuron. In another embodiment, the cell is a cardiac cell, including but not limited to, a myocyte. In another embodiment, the cell is an outer hair cell of the cochlear.

Therapeutic Treatment

The present disclosure also provides methods and compositions for modulating KCNQ channel activity in a subject in need thereof, by administering an effective amount of an agent that modulates the activity of a KCNQ channel or a subunit thereof. The present disclosure provides specific compositions containing at least one KCNQ channel binding molecule that modulates at least one KCNQ channel-mediated biological activity in an organism, including but not limited to, humans.

The dosage of an agent that is administered to a subject in need thereof may vary, depending on the reason for use and the individual subject. The dosage may be adjusted based on the subject's weight, the age and health of the subject, and tolerance for the compound or composition.

The amount of agent [therapeutic] to be used depends on many factors. Dosages may include about 2 mg/kg of bodyweight/day, about 5 mg/kg of bodyweight/day, about 10 mg/kg of bodyweight/day, about 15 mg/kg of bodyweight/day, about 20 mg/kg of bodyweight/day, about 25 mg/kg of bodyweight/day, about 30 mg/kg of bodyweight/day, about 40 mg/kg of bodyweight/day, about 50 mg/kg of bodyweight/day, about 60 mg/kg of bodyweight/day, about 70 mg/kg of bodyweight/day, about 80 mg/kg of bodyweight/day, about 90 mg/kg of bodyweight/day, about 100 mg/kg of bodyweight/day, about 125 mg/kg of bodyweight/day, about 150 mg/kg of bodyweight/day, about 175 mg/kg of bodyweight/day, about 200 mg/kg of bodyweight/day, about 250 mg/kg of bodyweight/day, about 300 mg/kg of bodyweight/day, about 350 mg/kg of bodyweight/day, about 400 mg/kg of bodyweight/day, about 500 mg/kg of bodyweight/day, about 600 mg/kg of bodyweight/day, about 700 mg/kg of bodyweight/day, about 800 mg/kg of bodyweight/day, and about 900 mg/kg of bodyweight/day. Routine experimentation may be used to determine the appropriate value for each patient by monitoring the compound's effect on KCNQ channel activity, or the disease pathology, which can be frequently and easily monitored. The agent can be administered once or multiple times per day. The frequency of administration may vary from a single dose per day to multiple doses per day. Preferred routes of administration include oral, intravenous and intraperitoneal, but other forms of administration may be chosen as well.

The effective amount of an agent according to the present disclosure may be administered along any of the routes commonly known in the art. This includes, for example, (1) oral administration; (2) parenteral administration, for example, by subcutaneous, intramuscular or intravenous injection; (3) topical administration; or (4) intravaginal or intrarectal administration; (5) sublingual or buccal administration; (6) ocular administration; (7) transdermal administration; (8) nasal administration; and (9) administration directly to the organ or cells in need thereof.

The effective amount of an agent according to the present disclosure may be formulated together with one or more pharmaceutically acceptable excipients. The active ingredient and excipient(s) may be formulated into compositions and dosage forms according to methods known in the art. These compositions and dosage forms may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

In the context of the present disclosure, the effective amount of the agent modulating KCNQ channel activity may be administered alone or in combination with one or more additional therapeutic agents (second therapeutic entity), regardless of the disease that said second therapeutic entity is administered to treat. In a combination therapy, the effective amount of the agent modulating KCNQ channel activity may be administered before, during, or after commencing therapy with another agent, as well as any combination thereof, i.e., before and during, before and after, during and after, or before, during and after commencing the additional therapy. For clarity, an agent of the present disclosure may be administered in an effective amount in response a prior treatment that brings about the need to modulate KCNQ channel function.

In another embodiment of the present disclosure the composition is a peptide that binds a KCNQ channel or a subunit thereof. In yet another embodiment of the present disclosure, said composition is a small molecule that functions in the same manner as a KCNQ channel effector, including but not limited to voltage, ATP, or $PIP_2$ to modulate KCNQ channel activity. In yet another embodiment, the agent is a nucleic acid. The nucleic acid may be an siRNA, shRNA. Nucleic acid molecules coding for any peptide that will interact with any of the amino acid sequences referenced herein, the expression vectors which include any of such nucleic acid molecules, as well as related host cells containing such nucleotide sequences or vectors, are also contemplated by the present disclosure.

Consistent with the observed properties of the KCNQ channels that are the subject of this disclosure, an agent of the present disclosure can be used to inhibit, suppress or cause the cessation of at least one KCNQ channel mediated disease pathology including but not limited to LQTS, epilepsy, deafness, atrial fibrillation and diabetes. See Unoki et al. *Nat. Genet.* 40:1098-102 (2008); and Holmkvist et al., *PLoS One.;* 4(6):e5872 (2009).

TERMINOLOGY

The term "KCNQ channel" or "KCNQ channels" is employed herein to refer any ion channel having at least one KCNQ subunit, including but not limited to KCNQ1, KCNQ2, KCNQ3, KCNQ4, and KCNQ5. Non-limiting examples of KCNQ channel(s) include $I_{Ks}$ channels, M-channels, and KCNQ4 channels.

The phrase "$I_{Ks}$ channel or $I_{Ks}$ channels" refers to any channel composed of KCNQ1 and KCNE1 subunits that form the basis of the slowly activating delayed-rectifier potassium current ($I_{Ks}$) that regulate cardiac action potential duration.

The phrase "M-channel" or "M-channels" refers to any channel composed of KCNQ2 and/or KCNQ3 subunits or KCNQ5 subunits that regulate neurotransmission and membrane excitability in neural cells.

The phrase "KCNQ4 channel" or "KCNQ4 channels" are composed of one or more KCNQ4 subunit and form the basis of the cochlear out hair cell and vestibular utricle $K^+$ currents ($I_{Kn}$).

The phrase "modulating the activity" or "modulating the level" is employed herein to refer to increasing the level or decreasing the activity of an entity including but not limited to, a channel, peptide or molecule. Non-limiting examples of the activity or level of a channel include the density (number of channels/unit area) of the KCNQ protein in a membrane or the ability of KCNQ channels to function or bind effectors thereof. The phrase "channel activity" or "channel function" refers to the ability of a channel to pass ionic current, small molecule(s), bind effectors, respond to voltage, mechanical force, heat, or light or regulate cellular homeostasis.

The term "channel" or "channels" as referred to in the present disclosure includes both 1) pumps that use a source of free energy including but not limited to, ATP, ionic gradient or light to drive the transport of ions or molecules across membranes within or surrounding cells of an organism; and 2) channels, which enable ions or molecules to flow through membranes within or surrounding cells.

The term "voltage dependent activation" refers to the process by which 1) a voltage-sensing domain of a KCNQ channel subunit moves from the resting to the activated state, for example a voltage sensing domain of the KCNQ1 protein moves to an activated state in response to membrane depolarization; 2) coupling, for example when a voltage-sensing domain of a KCNQ channel protein interacts with the channel pore (pore domain); and 3) opening of the channel pore.

The term "agent" is employed herein to refer to any kind of compound, molecule or ion and any combination thereof. In one embodiment of the disclosure the agent is a small molecule. In another embodiment of the disclosure, the agent is a biological molecule, including, but not limited to, a protein or a peptide or a nucleic acid, or an ion. In another embodiment, the nucleic acid is an interfering RNA.

The phrase "effector" or "effectors" refers to any small molecule, protein, ligand, or complex thereof that binds to, or interacts with a KCNQ channel or a subunit thereof. The result of this interaction may modulate a biological activity including but not limited to, muscle cell function, cell contractility, channel activation, neuronal discharge, membrane excitation, cell signaling, enzymatic activity, or protein-protein interaction.

The term "interfering RNA" is employed herein to refer to small interfering RNAs (siRNAs), short hairpin RNAs (shRNAs), microRNAs (miRNAs), antisense oligonucleotides, ribozymes, or any RNA-based molecule that interferes with the expression of a protein from its corresponding gene or modulate the activity of the protein.

In the context of this disclosure, the term "small molecule" refers to small organic compounds, including but not limited to, heterocycles, peptides, saccharides, steroids, antibodies and the like. The small molecule modulators preferably have a molecular weight of less than about 1500 Daltons, and more preferably less than 500 Daltons. The small molecules can be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), Microsource (New Milford, Conn.), and ChemBridge (San Diego, Calif.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The term "peptide" refers to a linear series of amino acid residues linked to one another by peptide bonds between the alpha-amino and carboxy groups of adjacent amino acid residues.

The term "synthetic peptide" is intended to refer to a chemically derived chain of amino acid residues linked together by peptide bonds. The term "synthetic peptide" is also intended to refer to recombinantly produced peptides in accordance with the present disclosure.

The phrase "subject in need thereof" as used herein refers to any organism in need of treatment, or requiring preventative therapy to prevent a condition resulting from lower or higher than normal levels of KCNQ channel activity in the organism, by the methods of the disclosure. The subject may be a plant or an animal. The subject animal includes fish, birds, or mammals. The subject may be livestock, such as cattle, swine, sheep, poultry, and horses, or pets, such as dogs and cats. In an embodiment of disclosure the subject is a human.

The term "effective amount" is employed herein to refer to the amount of an agent that is effective in modulating KCNQ channel activity in a subject or cell.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or stearic acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, $19^{th}$ Ed. Mack Publishing Company, Easton, Pa., (1995).

Excipients are added to the agent for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical agents that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid agent and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present disclosure, the modulator of a eukaryotic pathogen's adenylyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present disclosure may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present disclosure include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present disclosure, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present disclosure may be a capsule containing the composition, for example, a powdered or granulated solid composition of the disclosure, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting; however, they are not subjected to a final tableting step.

EXAMPLES

The following examples further illustrate the disclosure, but should not be construed to limit the scope of the disclosure in any way.

Example 1

Figure 2:
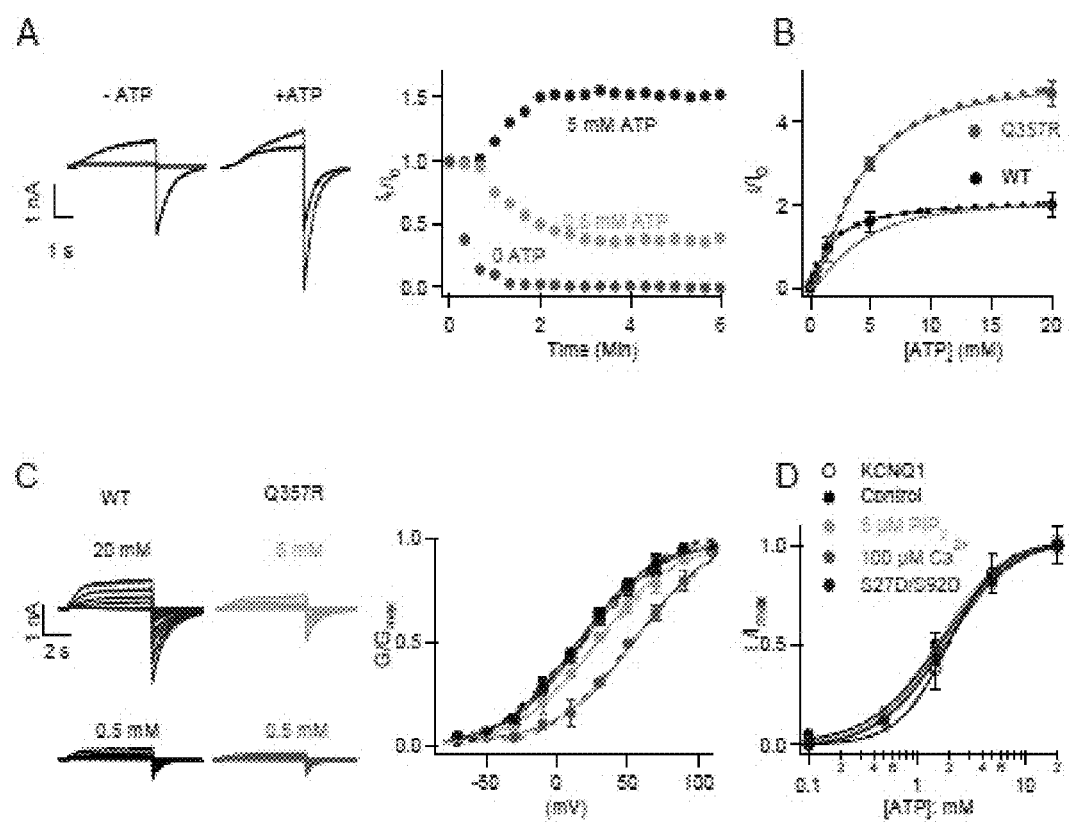
FIG. 2. ATP dependent activation of $I_{Ks}$ channels. (A) KCNQ1+KCNE1 ($I_{Ks}$) currents in inside-out patches rundown or run-up in 0 (red), 0.5 (green) and 5 (blue) mM ATP after patch excision. Voltage was stepped from a holding potential of −80 to +80 mV and then back to the holding potential. $I_t$ and $I_0$ in the right panel are tail current amplitudes. The current immediately after patch excision is black in left panels and $I_0$ in the right panel. (B) ATP dose response of WT (black) and Q357R (red) $I_{Ks}$. Solid curves are fits to the Hill equation with Hill coefficient 1 and 1.1, and $EC_{50}$ 1.66 and 9.60 mM for WT and Q357R $I_{Ks}$, respectively. Dashed curves are the fitting of the model in FIG. 4D. (C) Currents of WT (left) and Q357R (center) $I_{Ks}$ recorded from inside-out patches and G-V relations after patch excision in solutions containing various ATP concentrations. Solid curves are fits of Boltzmann Equation (see Methods) with $V_{1/2}$ and slope factor: WT, 25.2±2.5 mV, 25.6±1.4 (0.5 mM ATP, black); 23.6±3.6 mV, 27.8±2.2 (20 mM ATP, blue); Q357R: 53.2±2.5 mV, 27.3±1.3 (0.5 mM ATP, red); 28.8±2.6 mV, 26.4±2.1 (5 mM ATP, green). n=6 for all experiments. Dashed curves are the fitting of the model in FIG. 4D. (D) Normalized ATP dose-response of WT $I_{Ks}$ channel activation in control solution (black), 5 µM $PIP_2$ (green), 100 µM $Ca^{2+}$ (red), and S27D/S92D $I_{Ks}$ in control solution (blue). In control solution, $PIP_2$=100 µM and $Ca^{2+}$=0.5 nM. See Example 12. Five and 100 µM $PIP_2$ are 50% and 100% of saturation for $I_{Ks}$ channel activation, respectively.

$I_{Ks}$ Function Requires ATP $I_{Ks}$ currents were examined by inside-out membrane patches from Xenopus oocytes at various intracellular ATP concentrations. Upon patch excision, current ran down in low ATP (FIG. 2A), consistent with previous findings that the loss of native ATP in cytosol resulted in reduced channel activity. See Loussouarn G. et al., *EMBO J.* 22, 5412 (2003). However, the current ran up in the presence of higher concentrations of ATP, suggesting that not all the channels expressed in the membrane were active with the native cytosolic ATP that is insufficient to saturate channel activation. Thus, a reserve of the $I_{Ks}$ channels open in the presence of higher ATP concentrations, resulting in currents larger than that at the patch excision (FIG. 2A, B). The steady state current amplitude increased with ATP with the half maximal effective concentration ($EC_{50}$) at 1.7 mM (FIG. 2A, B), which is close to the physiological ATP concentration in cardiac myocytes. See Allen, D. G. et al., *J. Physiol* 361:185 (1985); Eisner, D A., et al., *J Physiol* 391:99 (1987); Stewart, L C., *J Mol Cell Cardiol* 26:1377 (1994). This result reveals that $I_{Ks}$ is sensitive to the cellular energetic state, and fluctuations of ATP such as in ischemia alters electrical properties via regulating $I_{Ks}$.

Example 2

The Physiological Importance of ATP Sensitivity of $I_{Ks}$

The physiological importance of $I_{Ks}$ is supported by our subsequent finding that Q357R in KCNQ1, a LQT-associated mutation identified in patients who presented arrhythmic episodes during physical exercise reduces ATP sensitivity, as shown by an increased EC50 of ATP response and the fraction of the currents activated by applied high ATP (FIG. 2B). Here it is shown that channels composed of Q357R co-expressed with KCNE1 (Q357R $I_{Ks}$) produces a smaller current amplitude, a slower activation time course and a shift of the voltage dependence of activation toward more depolarized potentials as compared with the WT $I_{Ks}$ channels measured from whole-cell currents. Each of these changes in channel properties decrease the contribution of $I_{Ks}$ to the termination of cardiac action potentials, resulting in prolongation of action potential duration. Furthermore, application of a high concentration of ATP during inside-out patch clamp recordings of Q357R $I_{Ks}$ restored the WT channel characteristics. Specifically, the current amplitude increased 3- to 5-fold, accounting for all of the reduction in the whole cell current and the voltage dependence of channel activation shifted back toward less depolarized voltages to nearly superimpose with that of the WT $I_{Ks}$ (FIG. 2C). These results show that a decrease in ATP sensitivity of the $I_{Ks}$ channel due to mutation Q357R leads to LQT-syndrome.

Example 3

KCNQ1 Expressed Alone without KCNE1 Shows a Similar Dose Response to ATP (FIG. 2D)

This shows that the ATP dependence is an intrinsic property of KCNQ1 and not altered by KCNE1 association. $I_{Ks}$ channels also require phosphatidylinositol 4,5-bisphosphate ($PIP_2$) for function and are modulated by calmodulin (CaM) and phosphorylation of residues S27 and S92 in KCNQ1 by protein kinase A (PKA). However, the response of $I_{Ks}$ currents to ATP did not change with reduced $PIP_2$, enhanced $Ca^{2+}$ or mutations S27D/S92D that mimic phosphorylation (FIG. 2D), indicating that ATP activates the channel independent from these other intracellular regulating molecules.

Example 4

Figure 3:
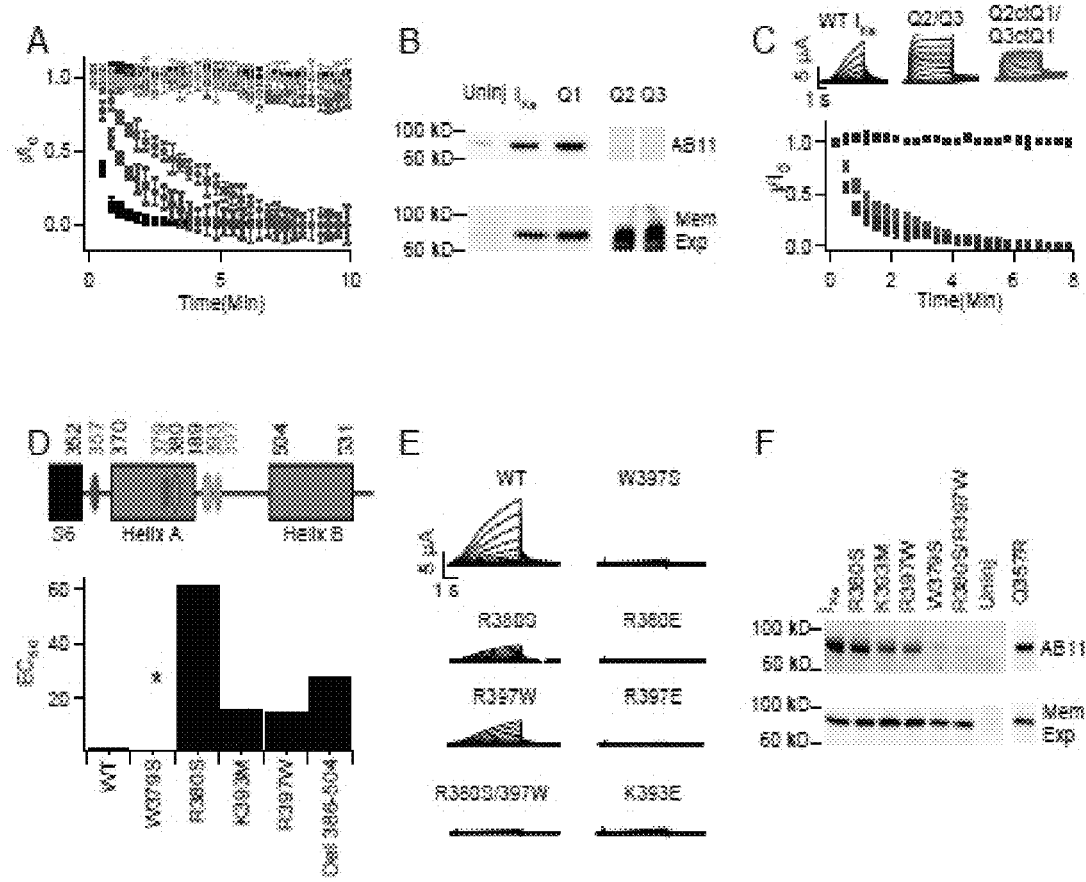
FIG. 3. ATP binding to KCNQ1. (A) $I_{Ks}$ current amplitude in intracellular solutions containing 1.5 mM of various nucleotides: ATP (blue), n=12, GTP (green), n=6; AMP-PNP (pink), n=4; ADP (red), n=4; AMP (purple), n=5; and no nucleotide control (black), n=6. The experimental protocol is the same as in FIG. 2A. (B) Western blot to detect AB11 labeling of channel proteins. Upper: channel proteins pulled down with avidin beads after UV light photo-cross-linking of the biotin-containing AB11. Bottom: channel proteins pulled down with avidin beads after biotin treatment of intact cells to detect expression in the membrane. Antibody against KCNQ1 was used in lanes with uninjected, $I_{Ks}$ and KCNQ1; antibodies against KCNQ2 and KCNQ3 were used in lanes with KCNQ2 and KCNQ3, respectively. (C) Whole-cell currents of WT and chimeric KCNQ1 and KCNQ2/KCNQ3 channels in response to depolarizing voltage pulses (top) and time dependence of current amplitude after inside-out patch excision without application of intracellular ATP (bottom). WT $I_{Ks}$ (black), n=6; WT KCNQ2/KCNQ3 (blue), n=3; Q2ctQ1/Q3ctQ1 (red), n=4. (D) Cartoon of the key region in KCNQ1 protein for ATP interaction (top), and $EC_{50}$ of ATP dose response of the key mutant $I_{Ks}$ channels. Asterisk: no current expression. (E) Whole-cell currents of interested mutations. (F) Western blot to detect AB11 labeling of interested channel proteins.

KCNQ Channels Formed by Coexpression of KCNQ2 and KCNQ3 do not Require ATP for Function ATP activates the $I_{Ks}$ channel by serving as the substrate for phosphorylation, binding to an associated protein or directly binding to the channel proteins. To distinguish these mechanisms, the ability of various nucleotides to prevent $I_{Ks}$ current run-down was measured. GTP and a non-hydrolyzable ATP analog, 5'-adenylyl-β-β-imidodiphosphate (AMP-PNP), in the intracellular solution sustained channel function as did ATP, while the rundown of $I_{Ks}$ currents became progressively faster when ADP and AMP were applied (FIG. 3A). Thus, ATP is not unique in activating the channel and phosphorylation is not required.

On the other hand, an ATP analog biotin photoprobe, 2-azidoadenosine 5'-triphosphate 2',3'-biotin-long chain-hydrazone (AB11) (see Conner, S D et al., *J Biol Chem* (2005) 280: 21539) can be photo-cross-linked to the KCNQ1 protein (FIG. 3B), indicating that the nucleotide directly binds to KCNQ1 to modify $I_{Ks}$ channel function. Here it is shown that the channels formed by co-expression of KCNQ2 and KCNQ3 do not require ATP for function (FIG. 3C), and AB11 cannot be photo-cross-linked to the KCNQ2 or KCNQ3 proteins (FIG. 3B).

Example 5

Location of the ATP Binding Cite in KCNQ1

To locate the ATP binding site in KCNQ1, chimera channels were analyzed by transplanting the cytosolic C-terminus to KCNQ2 and KCNQ3 to form Q2ctQ1 and Q3ctQ1. Similar to $I_{Ks}$ channels formed by the co-expression of Q2ctQ1/Q3ctQ1 ran down after inside-out membrane patch excision (FIG. 3C), suggesting that the chimeras acquire ATP sensitivity and the C-terminus of KCNQ1 contains the ATP binding site. Since the potency of nucleotides in activating Ic correlates with the number of phosphates (FIG. 3A) the channel associates with ATP through electrostatic interactions between basic residues and the negatively charged phosphates of ATP. A mutational scan was performed to neutralize each of all the basic residues in the intracellular loops and the C-terminus of KCNQ1 to examine which of these residues affected ATP sensitivity.

The results revealed three mutations, R380S, K393M and R397W, that reduced the expression of macroscopic $I_{Ks}$ currents and ATP sensitivity (FIG. 3D, E). Residue R380 is located in Helix A that is downstream from the S6 gate of the channel, whereas K393 and R397 are located in the linker between Helix A and Helix B (FIG. 3D). While each of these mutations reduced ATP sensitivity, a combined mutation R380S/R397W eliminated ionic current altogether, although channel expression in the plasma membrane could still be detected (FIG. 3E, F). Furthermore, R380S/R397W also eliminated photo-cross-linking of the ATP analog AB11 (FIG. 3F). These results show that these three residues are part of the ATP binding site, while each individual mutation reduces ATP binding, the combined mutations disrupt ATP binding, resulting in the loss of channel function. Likewise, mutating each of these residues to negatively charged amino acid residues, which could repel ATP, also eliminated ionic currents of $I_{Ks}$ (FIG. 3E). A Mutational scan of each aromatic residue in Helix A, B and the A-B linker identified one mutation, W379S, that eliminated ionic current and AB1 photo-cross-linking of $I_{Ks}$ (FIG. 3E, F), suggesting that W379 also participates in ATP binding. Interestingly, the mutations of the putative ATP binding site W379S, R380S, K393M and R397W are all associated with LQTS, further revealing the physiological importance of ATP modulation of $I_K$.

Example 6

Figure 4:
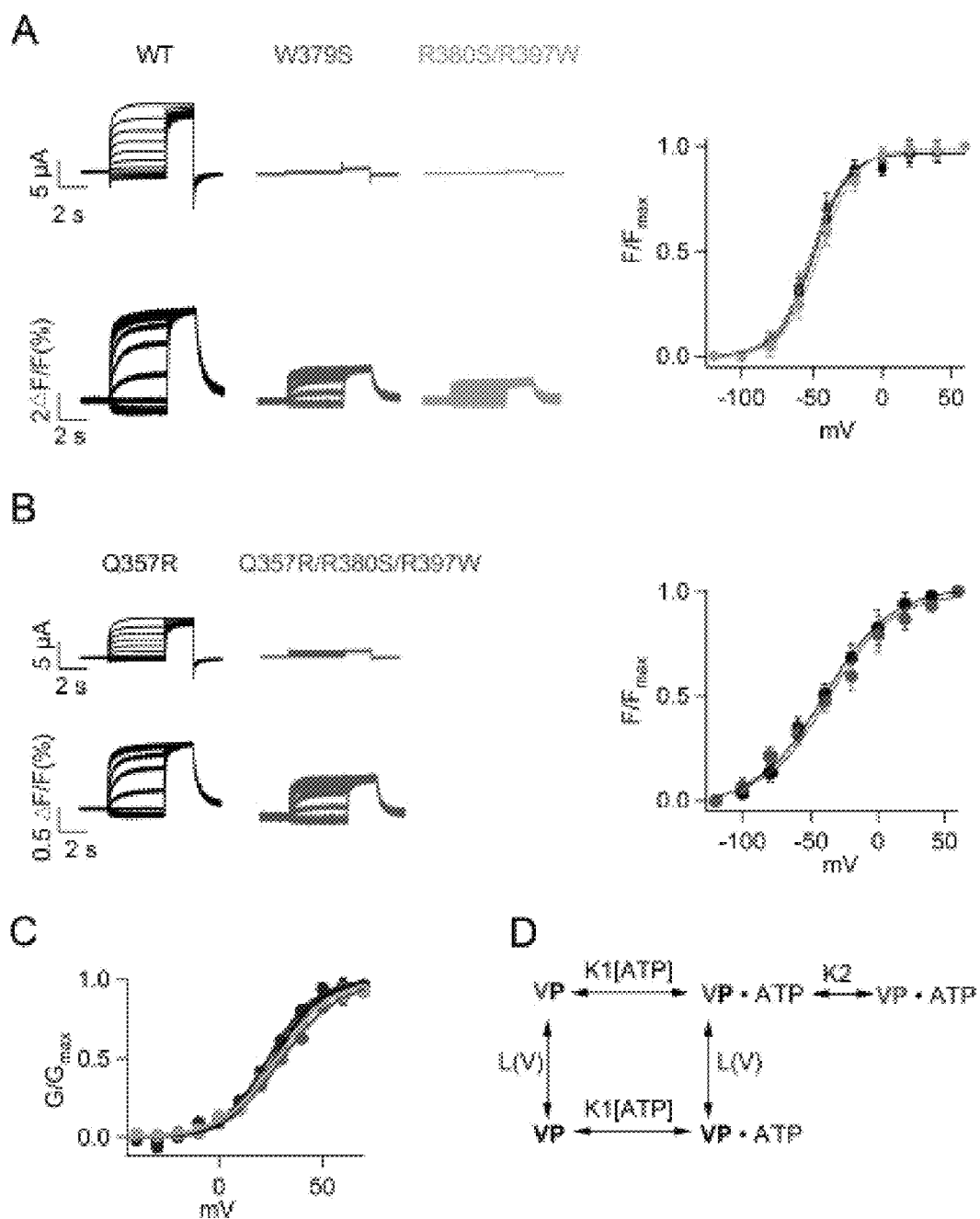
FIG. 4. ATP is required for pore opening. (A) Voltage clamp fluorometry (VCF) recordings of the WT and ATP-binding disruptive mutant $I_{Ks}$ channels. Left: whole-cell current (top) and fluorescence signal (bottom) of WT (black), W379S (red) and R380S/R397W (green) in response to a series of voltage pulses with increasing voltages. Right: steady-state fluorescence changes versus voltage (F-V). Smooth curves are Boltzmann fits to the data with $V_{1/2}$ and slope factor for WT, −50.4±1.2 mV, 14.6±0.9; W379S, −51.3±1.2 mV, 14.2±1.1; and S380S/R397W, 49.2±0.6 mV, 14.2±0.9. (B) Left: VCF recordings of Q357R (black) and Q357R/R380S/R397W (red). Right: F-V relations and Boltzmann fits with $V_{1/2}$ and slope factor for Q357R, −43.2±1.2 mV, 23.2±1.2; and Q357R/R380S/R397W, 44.1±0.8 mV, 22.1±0.9. (C) G-V relations of $I_{Ks}$ WT (black), R380S (green), K393M (blue), and R397W (red). Smooth curves are Boltzmann fits with $V_{1/2}$ and slope factor for WT, 26.4±1.2 mV, 11.2±0.9; R380S, 27.7±1.2 mV, 10.1±1.3; K393M, 25.4±1.1 mV, 10.9±1.1; and R397W, 30.7±1.2 mV, 14.1±1.3. (D) The scheme of voltage and ATP dependent activation of $I_{Ks}$ channels. In this conceptual model, voltage sensor movements are simplified as one transition between the resting (V black) and activated (V red) state, which is not affected by ATP binding; the transition of the pore from closed (P black) to the open (P red) state can happen only after voltage sensor activation and ATP binding. K1 and L(V) for the WT and Q357R $I_{Ks}$ obtained from fittings to ATP dose responses (FIG. 2B) and G-V relations at various ATP concentrations (FIG. 2C) are 300 $M^{-1}$ and $4.5 \times 10^{-4} \exp(0.94 VF/RT)$ (V: voltage, F: Faraday Constant, R: gas constant and T: absolute temperature), and K2 for WT and Q357R $I_{Ks}$ is 1287 and 350, respectively. For all experiments n=6-9.
Figure 5:
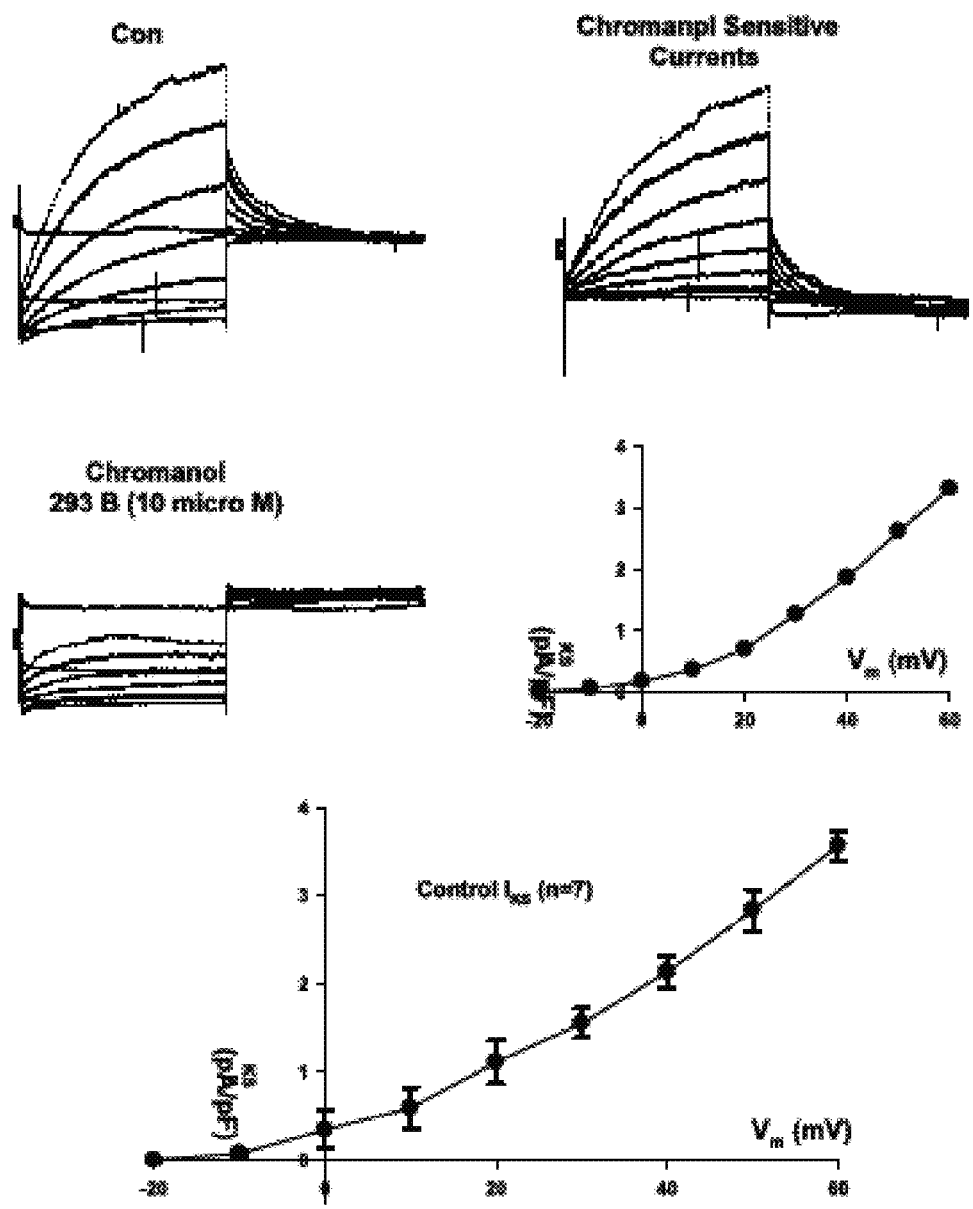
FIG. 5. Measurement of $I_{Ks}$ in guinea pig ventricular myocytes at 3 mM internal ATP. Time dependent currents are measured in the absence and presence of chromanol 293b, a blocker of $I_{Ks}$ channels. The current measurements are taken from control channels (Con, top left) and chromanol sensitive channels (top right) in the absence of chromanol 293b and in the presence of 3 mm internal ATP (Chromanol 293b (10 micro M), middle right).
Figure 6:
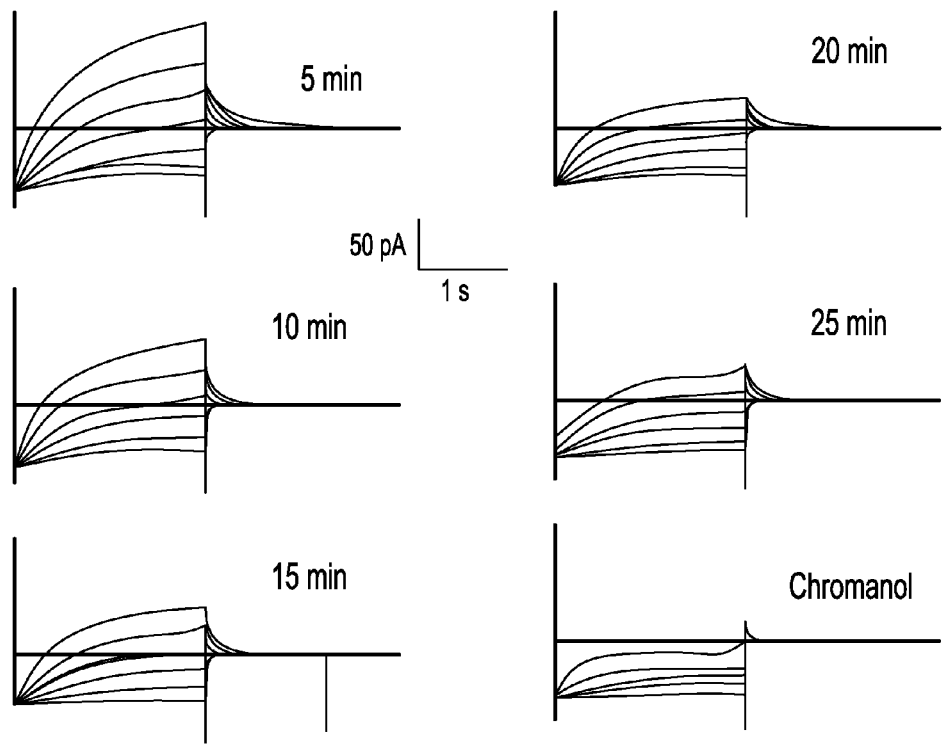
FIG. 6. Measurement of $I_{Ks}$ in guinea pig ventricular myocytes at 0 mM internal ATP. The chromanol 293b sensitive current is plotted as a function of time after patch formation. At all time points (5 min, top left; 10 min, middle left; 15 min, bottom left; 20 min, top right; 25 min, middle right) the chromanol 293b sensitive current is smaller than the chromanol sensitive current shown in FIG. 5 (top right) and current runs down in a time dependent manner.
Figure 6:
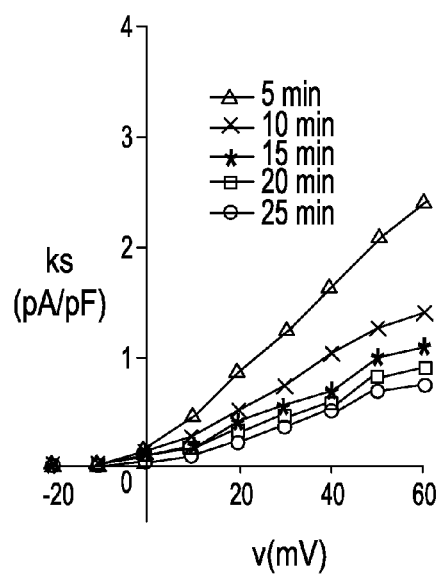
Figure 6:
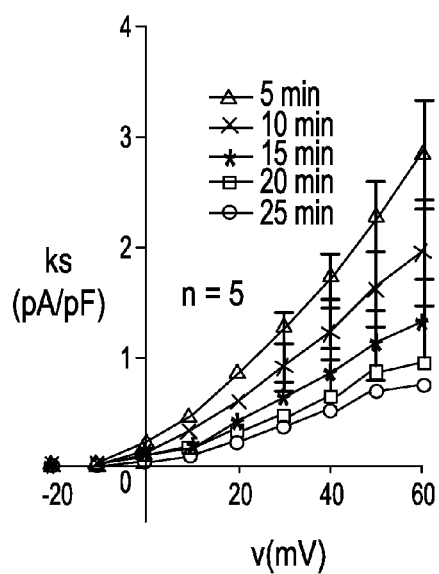
Figure 7:
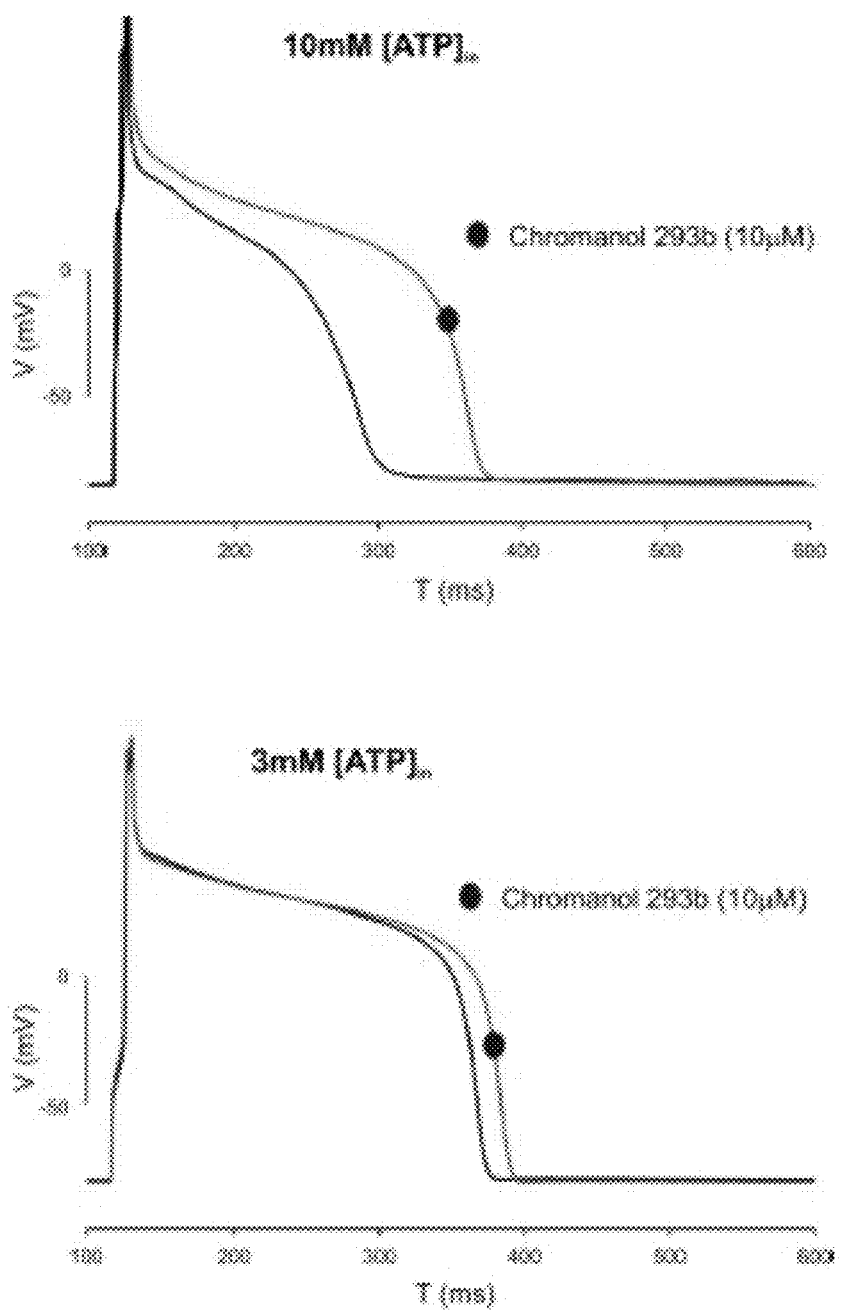
FIG. 7. Comparison of the action potentials of $I_{Ks}$ current in guinea pig ventricular myocytes at both 10 mM (top) and 3 mM (bottom) internal ATP concentrations (10 mM ATP concentration in the patch pipette solution, 3 mM ATP concentration in the patch pipette solution) in the presence and absence of chromanol 293b (closed circle). A higher concentration of ATP (top) shows a greater effect of chromanol 293b as shown by the shift in channel activity due to an increase in $I_{Ks}$ channel current density. Revealing that ATP shortens the ventricular action potential duration in cardiac myocytes.

ATP Binding Allows the Pore to Open and Co-Expression of KCNE1 does not Alter this Fundamental Mechanism of ATP Dependent Activation As a member of the Kv channel family, KCNQ1 is comprised of a voltage sensing domain (VSD) and a pore-gate domain (PD). The $I_{Ks}$ channel contains four KCNQ1 subunits with the VSD's surrounding a central pore across the membrane; in response to membrane depolarization, voltage sensors move to trigger pore opening. See Larrson et al., *PNAS* (2010). Voltage clamp fluorometry (VCF) was used to investigate whether ATP binding affects voltage sensor movements or pore opening; fluorescence signals from a fluorophore (Alexa 488 C5 maleimide) attached to VSD (see methods in Example 12, below) were recorded to monitor VSD movements, while ionic currents were simultaneously measured to show pore opening (FIG. 4A). The mutations that disrupt ATP binding, W379S and R380S/R397W (FIG. 3E), eliminated ionic currents of KCNQ1 but did not abolishΔF/F signals. Moreover, the F-V relationship is superimposed with that of the WT KCNQ1 (FIG. 4A), showing that ATP binding is not required for VSD movements but necessary for subsequent pore opening. These results lead to a conceptual model for ATP dependent activation of KCNQ1 and $I_{Ks}$ channels (FIG. 4D) such that ATP binding to the channel PGD is a prerequisite for the pore to open, but does not affect VSD activation. This experimental data of $I_{Ks}$-ATP dose response (FIG. 2B) and G-V relationship of $I_{Ks}$ at various ATP's (FIG. 2C) shows that the co-expression of KCNE1 does not alter the fundamental mechanism of ATP dependent activation. The lack of influence of KCNE1 on ATP dependent activation is also supported by the result that both KCNQ1 and $I_{Ks}$ channels showed a similar response to ATP (FIG. 2D).

Example 7

The Q357R Mutation does not Alter the Fundamental Mechanism of ATP Dependent Activation The disruption of ATP binding in the background of Q357R does not affect F-V relation (FIG. 4B). Q357 is located immediately C-terminal to the S6 gate in KCNQ1 and away from the amino acids cluster that are important for ATP binding (FIG. 3D), yet it causes a reduction in ATP sensitivity of $I_{Ks}$ activation (FIG. 2B). Although the WT $I_{Ks}$ activation requires ATP binding the properties of $I_{Ks}$ activation including steady-state G-V relation (FIG. 2C) and time course of voltage dependent activation and deactivation do not change with ATP, Q357R renders the G-V relation depending on ATP (FIG. 2C). While Q357R alters the slope of F-V relation as compared to the WT KCNQ1 (FIG. 4A, B), the mutation does not change the properties of $I_{Ks}$ G-V relation at high ATP (FIG. 2C), suggesting that a change in VSD movement may not relate to the change in ATP dependence of G-V relations. This reveals that all these changes are not brought by a direct influence of the mutation on ATP binding because unlike Q357R, mutations that directly affect ATP binding do not cause a shift of G-V relation to different voltages with the native ATP (FIG. 4C). Interestingly, a simple change in the equilibrium constant of pore opening in the model (FIG. 4D) can recapitulate the mutation-caused changes in ATP sensitivity (FIG. 2B) and ATP dependence of G-V relations (FIG. 2C). These results are consistent with the mechanism that ATP binding regulates pore opening and a change in pore open probability allosterically alters the ATP regulation. Since all of the reported mutations are associated with LQTS, these results show that mutations of KCNQ1 can alter ATP dependent activation of the $I_{Ks}$ channel with various mechanisms to cause human diseases.

Example 8

VSD Activation Occurs in the Absence of $PIP_2$

Using voltage-clamp fluorometry (VCF) on channels expressed in *Xenopus* oocytes, the effect of $PIP_2$ depletion on VSD activation and PD opening was determined simultaneously. In VCF, fluorescent labeling of the S3-S4 linker generates measurable changes in fluorescent intensity that are correlated with S4 movement during VSD activation; meanwhile, measurement of the whole cell ionic current detects PD opening. Here pseudo wild type (psWT)-C214A/G219C/C331A-Kv7.1 channels were used to avoid non-specific labeling of native C214 and C331 and labeled position G219C with Alexa 488 C5 maleimide. See Osteen, J D et al., *PNAS* 107:22710 (2010). To deplete $PIP_2$, CiVSP, a voltage-sensing lipid phosphatase that rapidly dephosphorylates $PIP_2$ upon membrane depolarization was expressed in cells according to the protocol provided in Murata, Y. et al., *Nature* 435:1239 (2005). When CiVSP was activated with a train of six depolarizing (+60 mV) pulses, the psWT channel current was robustly inhibited. In clear contrast, the magnitude of the fluorescence signal change ($\Delta F/F$) was unaltered by CiVSP, indicating that VSD activation still occurs after $PIP_2$ depletion. As an alternative method to VCF, VSD activation was analyzed using MTSES (2-sulfo-natoethyl methanethiosulfonate) modification of I230C in S4, which is only accessible to MTSES when the VSD is activated. See, for example, Murata Y, et al. (2005). This experiment confirmed that VSD activation occurs in the absence of $PIP_2$. After $PIP_2$ depletion, the steady-state voltage-dependence of VSD activation, reflected in the fluorescence-voltage (F-V) relationship, was unchanged, while the ionic currents were inhibited. Altogether, these results demonstrate that $PIP_2$ is not required for detection of membrane voltage within the VSD.

Example 9

$PIP_2$ is Required for Coupling

Applicants' tested whether $PIP_2$ is required for coupling. Coupling was quantified by measuring the effect of VSD activation on PD opening or by measuring how PD opening affects VSD activation. See Ryu, S., 140:469 (2012). This approach enables the measurement of VSD activation after $PIP_2$ depletion when PD opening became undetectable. In order to promote pore opening, the mutation L353K was introduced into the S6 gate. psWT/L353K channels conducted instantaneous current at every voltage we applied, and these currents were not reduced when we expressed and activated CiVSP. Furthermore, psWT/L353K currents reversed near $K^+$ equilibrium and were reduced when the Kv7.1 pore blocker chromanol 293B was applied according to the methods disclosed in Lerche, C. et al., 71:1503 (2007), which provides evidence that the observed constitutive currents were indeed conducted by expressed psWT/L353K channels. By comparing the VSD activation of psWT and locked open psWT/L353K channels VSD-PD coupling was detected directly as a leftward shift in the F-V relationship. This shift is consistent with the positive coupling between VSD activation and PD opening, i.e., less energy is required to activate the VSD if the PD is open. When $PIP_2$ was depleted using CiVSP, the psWT/L353K channels remained open, but their F-V relationship no longer differed from psWT channels. This showed that $PIP_2$ is required for PD opening (by L353K) to promote VSD activation.

Next other mutations were tested to determine whether $PIP_2$ is required to affect VSD activation and two such mutations (e.g., S349A, G350A) were identified. S349A, G350A, and L353 are located in the S6 gate, and homology modeling predicted that they do not interact with the VSD or the S4-S5 linker. This reveals that these mutations directly alter PD opening and indirectly affect VSD activation through $PIP_2$-dependent coupling. Thus, the data provided herein clearly show that $PIP_2$ is required both for VSD activation to cause PD opening and for PD opening to affect the activation of the VSD. Taken together, these findings show that a membrane lipid is required for the functional coupling between the VSD and the PD.

Example 10

Identification of the $PIP_2$ Binding Site

Figure 8:
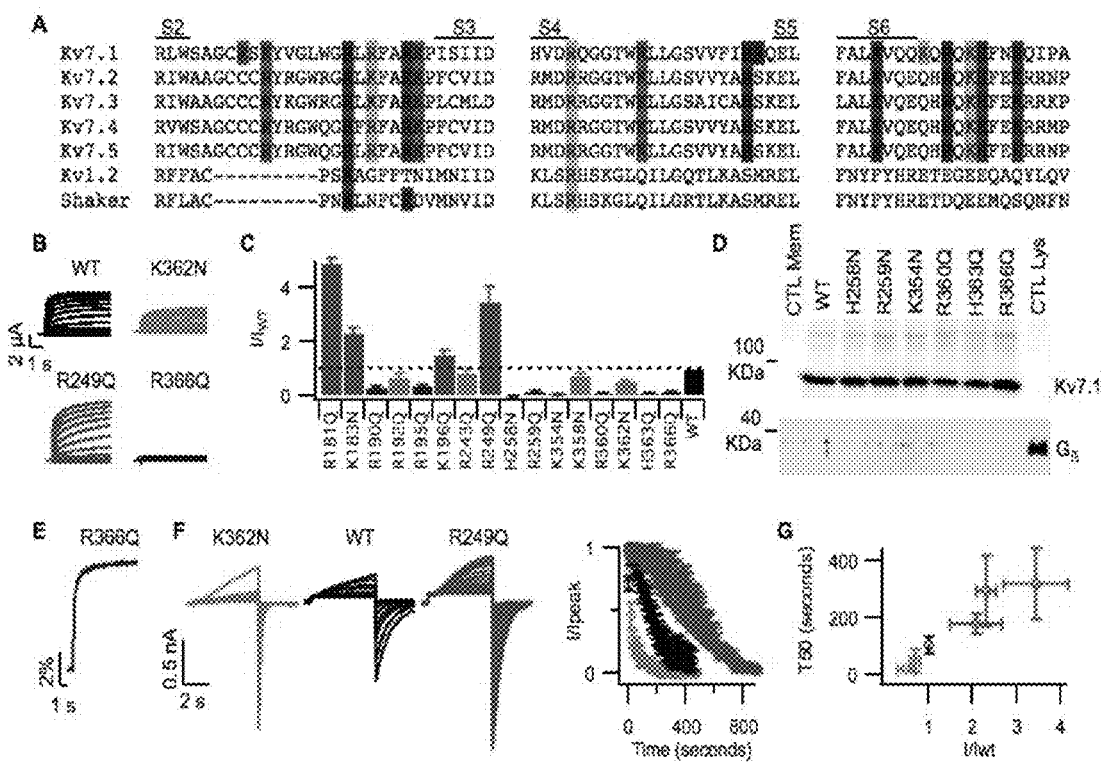
FIG. 8. Effects of mutations at the VSD-PD interface. (A) Sequence alignment of KCNQ channels S2-S3, S4-S5 linkers and proximal C-terminus. Highlighted residues were individually neutralized in WT KCNQ1 (Kv7.1). (B) Raw current at −100 to +40 mV. (C) Current amplitude (at +20 mV) normalized to WT. Color code: blue, I/Iwt<0.5; green, 0.5<I/Iwt<1; red, I/Iwt>1. (D) Western blot of biotinilated membrane proteins. CTL Mem, CTL Lys: membrane fraction and whole cell lysate from uninjected cells. (E) ΔF/F (−80 to +60 mV). (F) Current rundown after inside-out patch excision in the presence of KCNE1. Current in response to repeated +80 mV pulses (left). Normalized tail current amplitude (right). (G) 50% rundown time versus I/Iwt. From left to right: K362N, K358N, WT, R249Q, K183N, R249E.
Figure 9:
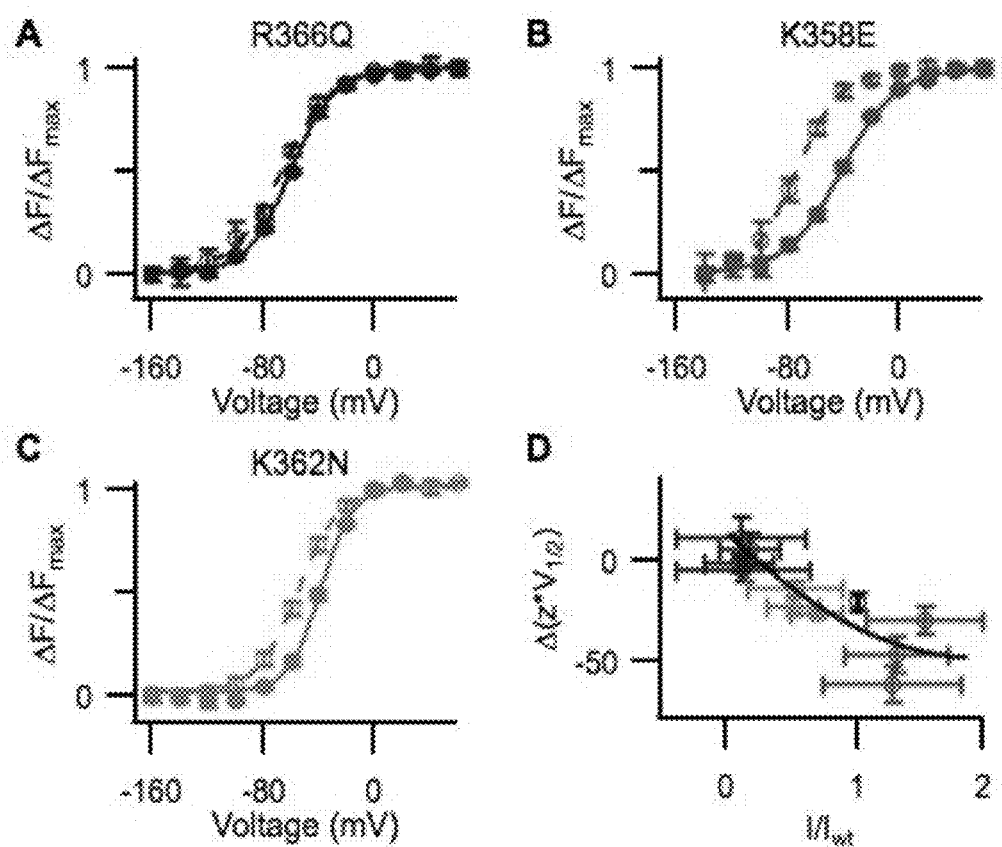
FIG. 9. Mutations at the VSD-PD interface alter coupling. Colors as in FIG. 8C. (A-C) F-V relationships of psWT/mutation (solid, filled) and psWT/L353K/mutation (dotted, open). (D) The change in $z^*V_{1/2}$ between psWT/mutation and psWT/L353K/mutation versus I/Iwt. From left to right: H363N, R195Q, R360Q, R366Q, K362N, R192Q, K358N, WT, K3358E, R360E, K196N. $z^*V_{1/2}$ is a measure of the energy required to activate the VSD, where z and $V_{1/2}$ were obtained by fitting the Boltzmann equation.
Figure 10:
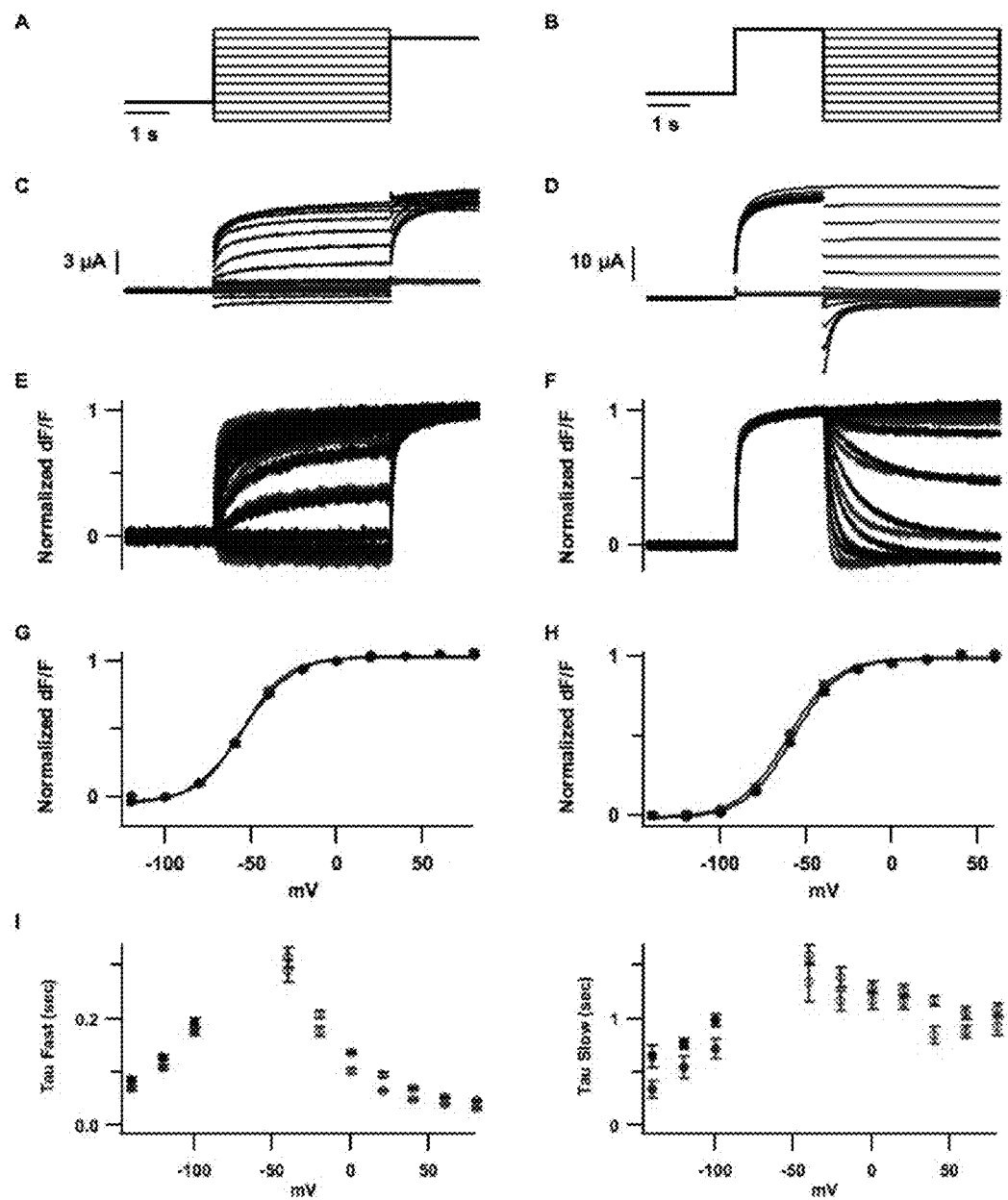
FIG. 10. Effects of $PIP_2$ depletion on voltage-dependent gating. VCF recordings of psWT (black) or psWT+CiVSP (blue). The protocols were designed to deplete $PIP_2$ in the presence of CiVSP by first applying six voltage pulses. (A) Voltage protocol used, the membrane potential is stepped from a holding potential of −80 mV to various test potentials (−120 to +80 mV) for 4 seconds and then to +60 mV for 2 seconds (−120 to +80 mV) for 4 seconds and then to +60 mV for 2 seconds to activate CiVSP. (B) The membrane is stepped from a holding potential of −80 mV to +60 mV for 2 seconds to activate the VSDs and CiVSP. The membrane potential is then repolarized to various test potentials (−140 to +60 mV) to track the return of the VSD to the resting state. (C, D) Raw Currents. (E,F) ΔF/F. Signals are normalized to that at the end of the +60 mV pulse (E) or prepulse (F). (G,H) Normalized F-V relationships. Signals at the end of the 4 s test pulses are normalized to that at 0 mV and plotted versus test voltage. (I) Fast (left) and slow (right) tau of the double exponential fit to the fluorescent signal changes caused by depolarization (−40 to +80 mV) or repolarization (−140 to −100 mV) are plotted versus test voltage.
Figure 11:
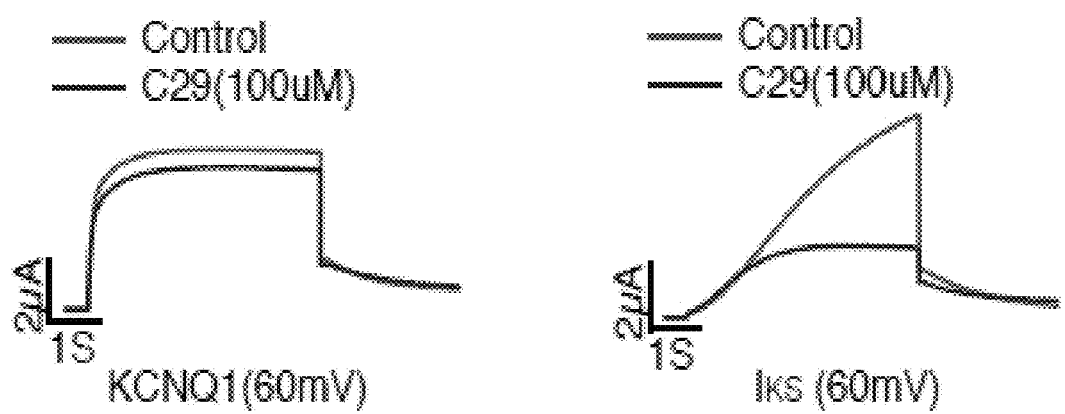
FIG. 11. Small molecule C29 selectively inhibits KCNQ channels composed of KCNQ1 and KCNE1. 100 μM concentrations of C29 inhibits $I_{Ks}$ channel current more effectively than KCNQ1 alone. Currents were induced by the application of a +60 mV pulse.
Figure 12:
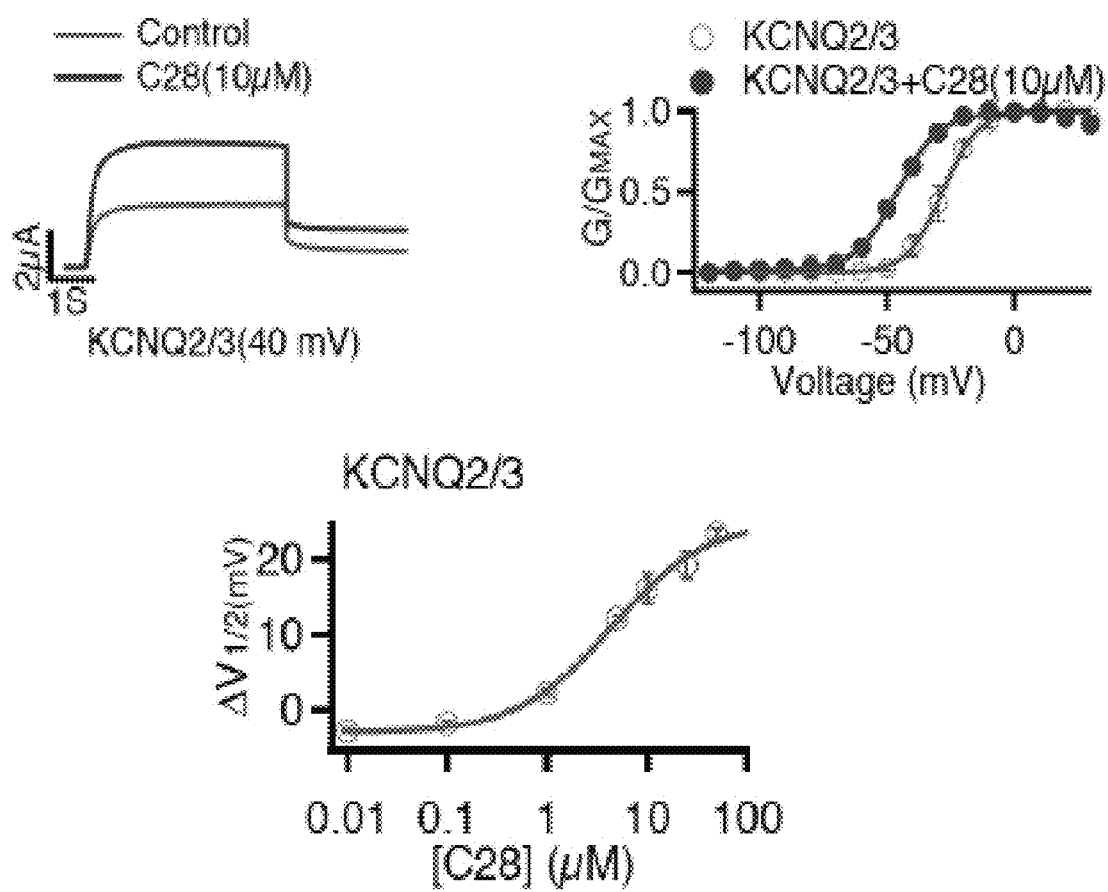
FIG. 12. Small molecule C28 modulates KCNQ channel activity. (A) C28 increases channel current in M-channels composed of KCNQ2 and KCNQ3 subunits. M-currents were measured at +40 mV, where G-V relation in the presence or absence of C28 is saturated. (B) The G-V relations in the presence or absence of C28. $V_{1/2}$ and the slope for KCNQ2/3 in the absence of C28 are −28.1±0.2 mV and 7.05±0.16 mV, respectively. $V_{1/2}$ and the slope for KCNQ2/3 in the presence of C28 are −45.9±0.4 mV and 8.21-0.37 mV, respectively. (C) The EC50 of the change in $V_{1/2}$ ($V_{1/2}$ control−$V_{1/2 C28}$) for KCNQ2/3 is 4.4±0.3 μM, and the Hill coefficient is 0.92±0.06.
Figure 13:
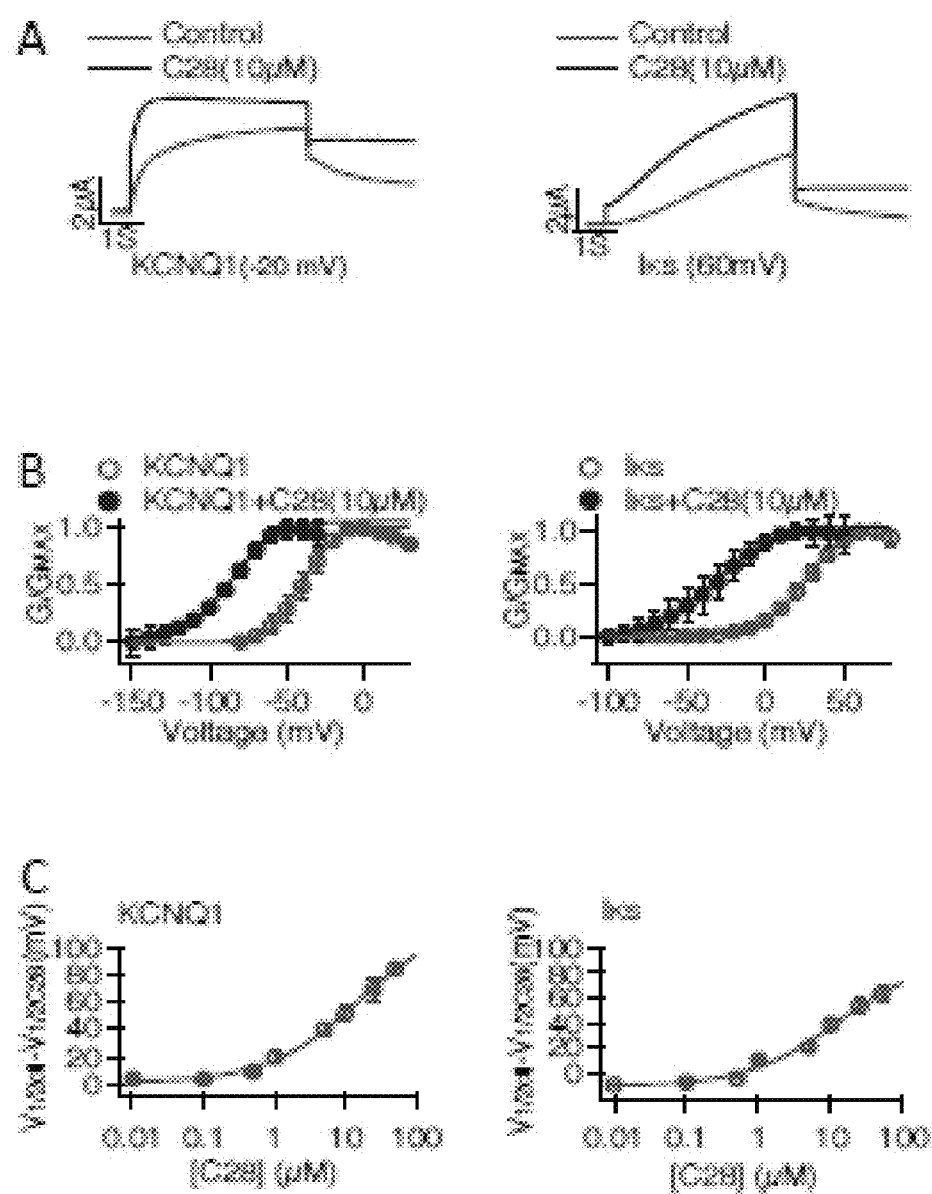
FIG. 13. Small molecule C28 modulates KCNQ1 and $I_{Ks}$ channel activity. (A) C28 increases current amplitudes. (B) C28 shifts G-V relations. The smooth curves are Boltzmann fit to data with $V_{1/2}$ and slope of −40.1±1.0 mV and 10.6±1.0 mV for KCNQ1 channels, and V in and a slope of −86.3±1.2 mV and 14.8±1.2 mV KCNQ1 channels with 10 M C28. The $V_{1/2}$ and slope is −23.9±0.9 mV and 12.9±0.8 mV for $I_{Ks}$ channels and $V_{1/2}$ and a slope of −32.2±1.0 mV and 18.9±1.1 mV $I_{Ks}$ channels in the presence of 10 μM C28. (C) Dose responses of G-V shift induced by C28. The EC50 of the change in $V_{1/2}$ ($V_{1/2}$ control−$V_{1/2 C28}$) for KCNQ1 is 15.8±8.5 μM, and 12.7±11.4 μM for $I_{Ks}$ channels. Taken together, C28 shifts $I_{Ks}$ in the negative direction in a dose dependent manner and is effective on both KCNQ1 and $I_{Ks}$.

A critical step to understanding how $PIP_2$ binding mediates VSD-PD coupling was to identify its binding site. Using a Kv7.1 homology model, 16 basic residues that are located near VSD-PD interface were identified. These residues are highly conserved among the Kv7 channels, which require $PIP_2$ for voltage-dependent gating, but are poorly conserved among other Kv channels that do not require $PIP_2$ (FIG. 8A). Using site directed mutagenesis, each of these basic residues in WT Kv7.1 were individually neutralized and the effect on the expressed current amplitude was measured using two-electrode voltage clamp. Because the endogenous level of $PIP_2$ in the oocyte membrane is within the sensitive range of Kv7.1 a reduction of $PIP_2$ sensitivity by any mutation is will reduce Kv7.1 currents. The data reveal that eight mutations (R190Q, R195Q, H258N, R259Q, K354N, R360Q, H363N, R366Q) severely decreased (>50% reduction, FIG. 8B, C blue) the whole cell current amplitude and four mutations (R192Q, R243Q, K358N, K362N) that had a milder reduction (<50% reduction, FIG. 8B,C green). Conversely, four neutralizing mutations (R181Q, K183N, K196N, R249Q) and three additional charge-reversing mutations (R249E, K358E, R360E) actually increased the current amplitude (FIG. 8B, C, red). Notably, robust surface expression of the loss-of-current mutants by Western Blot analysis of proteins labeled by extracellular biotin (FIG. 8D) was detected showing that loss of current expression is not due to reduced protein synthesis or membrane trafficking. Furthermore, fluorescent signal changes in VCF measurements for all of the loss-of-current mutations (FIG. 8E, 9) were observed indicating that these mutant channels not only expressed to the membrane, but also retained VSD activation. Therefore, the loss-of-current mutations affected channel gating by decreasing coupling is consistent with decreased $PIP_2$ binding, or by decreasing PD opening.

Next, the mutations identified were examined for their ability to affect current amplitude by changing the apparent $PIP_2$ affinity. Applicants' measured the time course of the current rundown that occurs spontaneously as phosphoinositides are lost from excised membrane patches. Applicants' found that the effects of mutations (K358N, K362N, R181Q, K183N, R249Q, R249E) on the time course of rundown after patch excision were correlated with their effects on expressed current amplitude. That is, relative to WT channels, the rundown was faster for the mild loss-of-current mutations and slower for the gain-of-current mutations (FIG. 8F-G). These results further support the finding that the mutations of conserved basic residues at the VSD-PD interface affect a $PIP_2$ mediated process that is required for channel function.

Next, the strength of VSD-PD coupling for several of the mutations identified herein was directly quantified including, but not limited to, R192Q, R195Q, K196E, K358N, K358E, R360Q, R360E, K362N, H363N, R366Q by measuring the F-V shift caused by locking the PD open with L353K. The mutations influenced VSD-PD coupling in a manner that was correlated with their effect on the expressed current amplitude i.e., the loss-of-current mutations decreased the magnitude of the F-V shift, while the gain-of-current mutations increased the F-V shift (FIG. 9A-D). Strikingly, the equilibrium model predicted this relationship when the binding constant for $PIP_2$ ($K_{PIP2}$) (FIG. 9 D, black line) was varied. Taken together, these results suggest that these mutations disrupt VSD-PD coupling and decrease channel current by directly affecting $PIP_2$ binding.

Applicants mapped these data onto a Kv7.1 homology model and found a cluster of severe loss-of-current residues at the VSD-PD interface that includes R190 and R195 in the S2-S3 linker, H258 and R259 in the S4-S5 linker, and K354 in the proximal C terminus. In the experiments herein, these mutations mimicked the effects of $PIP_2$ depletion on psWT channels: they severely inhibited the ionic current, did not prevent VSD activation, and greatly diminished the VSD-PD coupling. Therefore, this cluster of basic residues constitutes a critical interaction site for $PIP_2$ mediated coupling. These findings show that applicants have identified site is a $PIP_2$ binding site that is conserved among voltage-dependent and voltage-independent $K^+$ channels.

$PIP_2$ mediated coupling in Kv7.1 has direct implications for human pathophysiology. In the heart, Kv7.1 subunits coassemble with KCNE1 accessory subunits to generate the slow delayed rectifier current ($I_{Ks}$) that regulates the duration of the cardiac action potential. Inherited loss-of-function mutations of Kv7.1 and KCNE1 are associated with Long-QT Syndrome (LQTS), in which the ventricular action potential duration is prolonged, resulting in a high risk of ventricular arrhythmias and sudden death. Many LQTS associated mutations affect the basic residues in the $PIP_2$ pocket for example, R190Q, R190W, 258N, H258R, R259H, R259C, R259L, R360T, R366Q, R366W, R366P. For these mutations, loss of VSD-PD coupling compromises the $I_{Ks}$ channel function and create a substrate for cardiac arrhythmias. The results demonstrate that modifiers of VSD activation will not rescue channel function for these mutations. Furthermore, drugs that force the PD open will abolish the voltage- and time-dependence of the $I_{Ks}$ current that is critical for the timing of the action potential. Thus, a drug that targets $PIP_2$ dependent coupling amplifies current without losing these physiologically important characteristics.

Example 11

Figure 1:
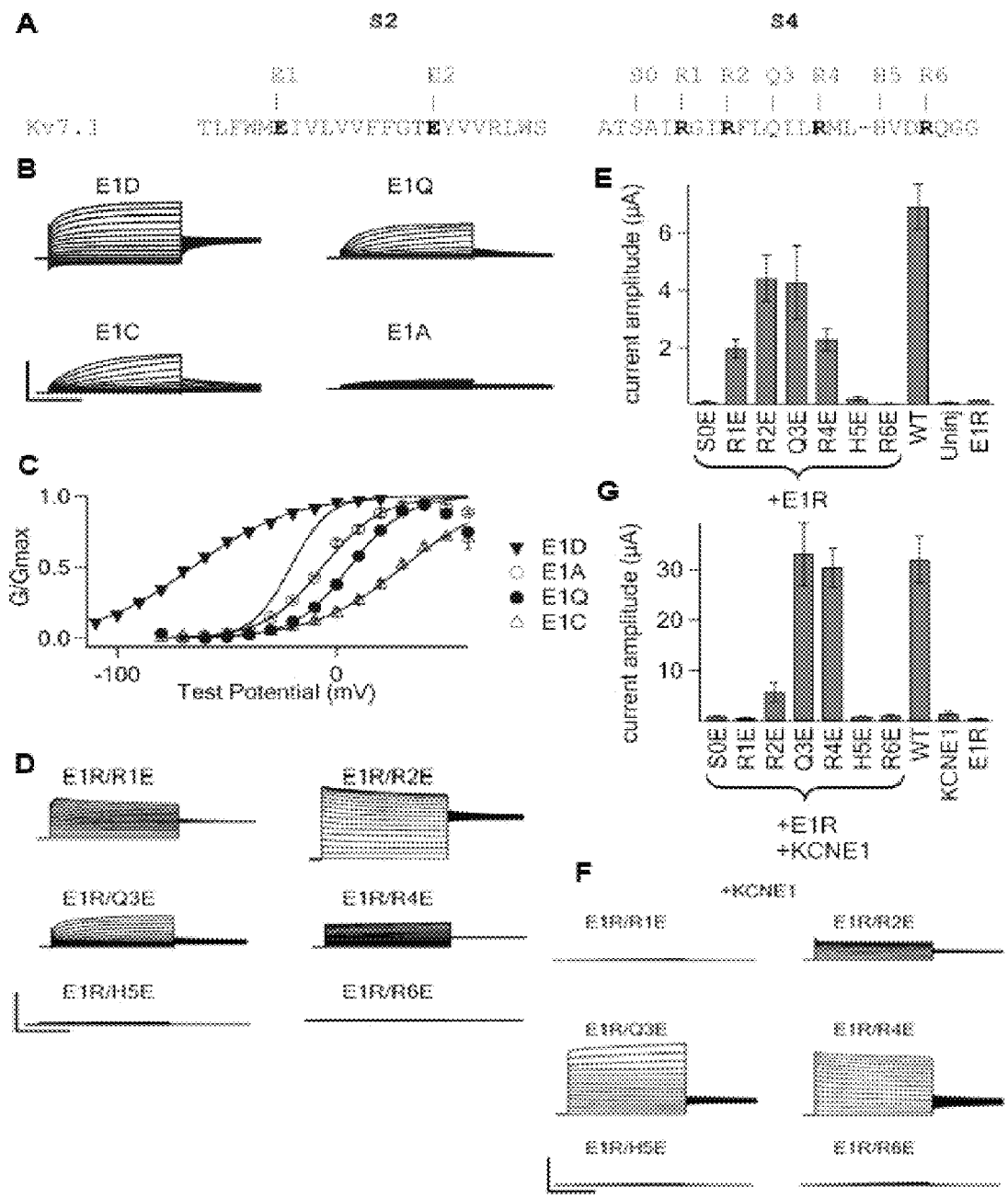
FIG. 1. (A) Sequence of S2 and S4 amino acid domains comprising the voltage gating sensor domain of $I_{Ks}$ channel showing conserved negatively charged amino acid residues in S2 and positively charged residues in S4 (bold). (B) Currents from various E1 mutations to negative or neutral residues in $I_{Ks}$ channels (Scale: 4 µA). (C) G-V relationship from mutations in (C). Gray line represents WT $I_{Ks}$. Error bars represent standard error of the means. (D) S4 mutations to glutamate restore E1R current. Currents were recorded from double mutations (Scale: 6 µA). (E) Peak current amplitudes in (A) were averaged for each mutation. Error bars represent standard error of the means. (F) Current from E1R paired with S4 residues mutated to glutamate coexpressed with KCNE1 (Scale: 20 µA). (G) Peak current amplitudes in C were averaged for each mutant. Error bars represent standard error of the means. See Wu, D. et al., *J. Gen. Physiol.*, (2010) 135: 595-606.

Voltage Dependent Activation is Sensitive to Charge Perturbations at the E1 Position Like most voltage-dependent channels, Kv7.1 contains two conserved glutamates in S2 (E1 and E2) and a series of arginines in S4 (R1, R2, etc.) (FIG. 1A). However, Kv7.1 has a glutamine (Q3) at what is the third arginine position and a histidine (H5) at what is the fifth arginine position in other Kv channels. Applicants found that E1K or E1K+KCNE1 generates current indistinguishable from background current expressed by native oocyte channels without or with KCNE1 (<0.5 or <2 µA, respectively), and much smaller than wild-type (WT) Kv7.1 or WT Kv7.1+KCNE1 currents, revealing that E1K channels themselves do not generate any current. A similar charge reversal mutation, E1R, exhibits an identical phenotype to E1K. When E1 was conservatively mutated to the negatively charged aspartate or mutated to the electrically neutral glutamine, cysteine, or alanine, all formed functional channels, although E1A reduced current (FIG. 1B). Neutralizing mutations all shifted the G-V relationship rightwards (FIG. 1C), revealing that removal of the negative charge at E1 hinders channel activation. Only a positive charge at E1 completely abolished current. These results show that the loss of current is caused by the inability of E1K/R channels to open, through disruption of electrostatic interactions involving E1 and not due to a trafficking defect.

Inspection of the sequence of Kv7.1 and KCNE1 reveals that the arginines in the S4 segment of Kv7.1 are the only positively charged residues in the membrane-spanning segments. E1R paired with R1E, R2E, Q3E, or R4E generated currents significantly larger than currents from E1R alone (FIG. 1D, E). While, S0E, H5E, and R6E that flank these four residues could not rescue any current (FIG. 1E). These data show that E1 interacts electrostatically not only with R4, but also with R1 and R2. Q3 is also positioned to interact with E1 through hydrogen bonding in native channels. Restoring electrostatic attractions between specific residues and E1R allows S4 to occupy an activated conformation so that channels can open, albeit with properties different from WT channels. All the rescued currents except for E1R/Q3E changed instantaneously in response to voltages from −120 to +60 mV (FIG. 1D). These currents have reversal potentials that approach the $K^+$ equilibrium potential (80-90 mV) and are be blocked by the Kv7.1 pore-blocker chromanol 293B, confirming that these are $K^+$ currents carried through the conduction pore of constitutively open channels.

Example 12

Materials and Methods

Mutagenesis.

Site-directed mutations were introduced using overlap extension and high fidelity PCF. DNA sequencing confirmed each mutation. RNA was made by in vitro transcription using the mMessage mMachine T7 polymerase kit (Applied Biosystems).

Channel Expression.

9.2 ng of channel cRNA was injected, using Nanoject (Drummond), into each of stage V-VI, defolliculated oocytes from *Xenopus laevis*. For expression of CiVSP, 2.3 ng of CiVSP RNA was injected simultaneously. The cells were incubated at 18° C. for 4-7 days for robust expression in ND96 solution [in mM: 96 NaCl, 2 KCl, 1.8 $CaCl_2$, 1 $MgCl_2$, 5 HEPES, 0.3 K2EDTA].

Electrophysiology.

Two-electrode voltage clamp: Whole-cell currents were recorded from oocytes bathed in ND96 solution using a CA-B amplifier (Dagan) in two-electrode voltage clamp mode. Microelectrodes were pulled to a resistance of 0.3-3 MΩ and filled with 3 mM KCl. Signals were sampled at 1 KHz using the Patchmaster acquisition software (HEKA). The holding potential was set to −80 mV throughout unless otherwise specified.

Voltage-clamp fluorometry: For VCF, oocytes were labeled on ice for 45 minutes in 10 µM Alexa 488 C5 Maleimide (Life Technologies) in high potassium depolarizing solution [in mM: 98 KCl, 1.8 CaCl2, 1 MgCl2, 5 HEPES, PH 7.6]. The cells were washed with ND96 and kept on ice until VCF recording. Fluorescent signals were recorded simultaneously with the whole cell (TEVC) currents in ND96 solution, using a DLMFS (Leica) upright microscope through a FITC filter cube (Lieca). Light from a standard 100W halogen bulb was focused onto the animal pole of the oocyte and emission from the cube was focused on a P20A photodiode. The current from the photodiode was amplified using an EPC10 patch amplified (HEKA), low pass filtered at 200 Hz and sampled at 1 KHz using Patchmaster (HEKA).

Patch clamp: Inside-out membrane patches were formed using patch electrodes pulled to 0.5-1 MΩ and filled with pipette solution [in mM: 140 KMeSO3, 20 HEPES, 2 KCl, 2 MgCl2, PH 7.2] and excised into the bathing solution [in mM: 140 KMeSO3, 20 HEPES, 2 KCl, 5 EGTA, 1.5 mM MgATP, PH 7.2]. Macroscopic currents were recorded, at room temperature, using an Axopatch 200-B amplifier (Axon Instruments) driven by the Pulse (HEKA) acquisition software. Current were digitized at 1 KHz. All recordings were made in room temperature (20-22° C.).

Data Analysis.

The baseline fluorescence was fit with a line during the 2 seconds at the −80 mV holding potential that preceded each test pulse. This linear baseline approximation was extrapolated to the duration of the pulse and $\Delta F/F$ was calculated as $(F(t)-F_{baseline}(t))/F_{baseline}(t)$ where $F(t)$ is the fluorescent intensity at time t (AU) and $F_{baseline}(t)$ is the extrapolated baseline value at time t. The Boltzmann equation was used to fit the fluorescence-voltage relationships: Normalized $\Delta F(V)=PVa(V)=1/(1+\exp(-z*F*(V-V_{1/2})/RT)$ where PVa is the voltage-dependent probability of the voltage sensor assuming the activated state, V is the test voltage (V), $V_{1/2}$ is the voltage of half maximal voltage sensor activation, z is the number of elementary charges translocated across the membrane upon VSD activation, R is the gas constant (J/K/mol), and F is the faraday constant (C/mol).

Chemical Modification.

2-sulfo-natoethyl methanethiosulfonate (MTSES, Toronto Research Chemicals) was dissolved in DMSO at 100 mM, aliquoted and frozen immediately. Aliquots were thawed just prior to use and added directly to bath solution in a bolus to achieve the desired final concentration.

Biotinylation:

Membrane expression was detected through biotinylation and Western blot (see Wu et al., *Journal of General Physiology*. (2010)). Cell surface proteins of intact oocytes were labeled with 1 mg/ml of Sulfo-NHS-SS-Biotin (Thermo Scientific). The cells were washed, homogenized, and incubated with Neutravidin beads (Thermo Scientific) to pull down biotin labeled proteins. The pulled down proteins were probed via Western blot using a Kv7.1 antibody (Santa-Cruz Biotechnology) or a GP antibody to test for labeling of cytosolic proteins.

What is claimed is:

1. A method of treating Long-QT syndrome ("LQTS") in a subject in need thereof comprising administering an effective amount of an agent that modulates the activity of a KCNQ channel, wherein said agent is C28.

2. The method of claim 1, wherein said KCNQ channel is an $I_{Ks}$ channel.

3. The method of claim 2, wherein the agent modulates $I_{Ks}$ channel activity by altering voltage dependent activation of the $I_{Ks}$ channel.

4. The method of claim 1, wherein said KCNQ channel is an M-channel.

5. The method of claim 4, wherein the agent modulates M-channel activity by altering voltage dependent activation of the M-channel.

6. The method of claim 1, wherein said KCNQ channel is KCNQ4 channel.

7. The method of claim 6, wherein the agent modulates KCNQ4 channel activity by altering voltage dependent activation of KCNQ4 channels.

8. The method of claim 1, wherein the agent modulates KCNQ channel activity by altering ATP binding to the KCNQ channel.

9. The method of claim 8, wherein the agent modulates KCNQ channel activity by altering ATP binding to the KCNQ channel by interacting directly with a segment of the KCNQ1 protein comprising the amino acid sequence set forth in SEQ ID NO: 25.

10. The method of claim 1, wherein the agent modulates KCNQ channel activity by altering $PIP_2$ binding to the KCNQ channel.

11. The method of claim 1, wherein the agent increases KCNQ channel activity.

12. The method of claim 1, wherein the agent reduces KCNQ channel activity.

* * * * *